United States Patent
Shi et al.

(10) Patent No.: US 9,802,907 B2
(45) Date of Patent: Oct. 31, 2017

(54) 2-ARYL SELENAZOLE COMPOUND AND PHARMACEUTICAL COMPOSITION THEREOF

(71) Applicant: JIANGSU ATOM BIOSCIENCE AND PHARMACEUTICAL CO., LTD., Zhenjiang (CN)

(72) Inventors: Dongfang Shi, Zhenjiang (CN); Changjin Fu, Zhenjiang (CN); Jie Wu, Zhenjiang (CN); Jun Liu, Zhenjiang (CN)

(73) Assignee: JIANGSU ATOM BIOSCIENCE AND PHARMACEUTICAL CO., LTD., Zhenjiang (CN)

( * ) Notice: Subject to any disclaimer, the term of this patent is extended or adjusted under 35 U.S.C. 154(b) by 0 days.

(21) Appl. No.: 14/648,664

(22) PCT Filed: Nov. 24, 2013

(86) PCT No.: PCT/CN2013/087736
§ 371 (c)(1),
(2) Date: May 29, 2015

(87) PCT Pub. No.: WO2014/082548
PCT Pub. Date: Jun. 5, 2014

(65) Prior Publication Data
US 2015/0291543 A1   Oct. 15, 2015

(30) Foreign Application Priority Data
Nov. 30, 2012   (CN) .......................... 2012 1 0504310

(51) Int. Cl.
| | |
|---|---|
| *C07D 293/06* | (2006.01) |
| *C07D 421/10* | (2006.01) |
| *A61K 31/381* | (2006.01) |
| *A61K 33/04* | (2006.01) |
| *A61K 31/41* | (2006.01) |
| *A61K 31/4365* | (2006.01) |
| *A61K 31/4439* | (2006.01) |
| *A61K 31/496* | (2006.01) |
| *A61K 31/5377* | (2006.01) |
| *C07D 421/12* | (2006.01) |
| *C07D 495/04* | (2006.01) |

(52) U.S. Cl.
CPC ............ *C07D 293/06* (2013.01); *A61K 31/41* (2013.01); *A61K 31/4365* (2013.01); *A61K 31/4439* (2013.01); *A61K 31/496* (2013.01); *A61K 31/5377* (2013.01); *C07D 421/10* (2013.01); *C07D 421/12* (2013.01); *C07D 495/04* (2013.01)

(58) Field of Classification Search
CPC .. C07D 293/06; C07D 421/10; A61K 31/381; A61K 33/04
USPC .......................................... 548/100; 514/183
See application file for complete search history.

(56) References Cited

FOREIGN PATENT DOCUMENTS

| CN | 103130744 A | * | 6/2013 | ............ C07D 293/06 |
|---|---|---|---|---|
| KR | WO 2011105643 A1 | * | 9/2011 | ............ A61K 31/095 |

* cited by examiner

*Primary Examiner* — Matthew Coughlin
*Assistant Examiner* — Sagar Patel
(74) *Attorney, Agent, or Firm* — Oliff PLC

(57) ABSTRACT

A 2-aryl selenazole compound and a pharmaceutical composition are disclosed, wherein the 2-aryl selenazole compound is a compound represented by formula (I) or a pharmaceutically acceptable salt thereof. The 2-aryl selenazole compound has the activity of inhibiting xanthine oxidase. The compound or a pharmaceutically acceptable salt thereof can be applied in terms of preparing a drug used for prevention or treatment of hyperuricemia, gout, diabetic nephropathy, an inflammatory disease or a neurological disease.

21 Claims, No Drawings

2-ARYL SELENAZOLE COMPOUND AND PHARMACEUTICAL COMPOSITION THEREOF

This application is the U.S. national phase of International Application No. PCT/CN2013/087736 Filed on 24 Nov. 2013 which designated the U.S. and claims priority to Chinese Application Nos. CN201210504310.8 filed on 30 Nov. 2012, the entire contents of each of which are hereby incorporated by reference.

BACKGROUND

Technical Field

The present invention relates to the field of medicinal chemistry, and in particular, to a 2-aryl selenazole compound and application thereof. The present invention further relates to a method for preparing the compound, a pharmaceutical composition including the compound, and medical uses thereof, especially application as a xanthine oxidase inhibitor in treatment of gout and hyperuricemia.

Related Art

Gout is a disease caused by deposition of sodium urate in vivo when an excessively great amount of uric acid is generated due to disorder of purine metabolism in vivo. Gout is a second largest metabolism disease following diabetes, and has been listed by UN as one of the twenty most chronic and stubborn diseases in $21^{st}$ century. According to epidemiological studies at home and abroad, with improvement of living level and increase of average lifetime of human beings, the incidence of hyperuricemia and gout shows an increasing tendency. It was reported that, during ten years from 1990 to 1999, the incidence of gouty arthritis in U.S. was increased from 0.29% to 0.52% (Arthur L. Weaver. Epidemiology of gout [J]. Cleveland Clinic Journal of Medicine 2008, 75 (Suppl 5): S9-S12); in a national health investigation carried out between 2007 and 2008, 8.3 million Americans reported that they were informed by their doctors that they suffered from gout; and the incidence thereof in UK and German was 1.4% during a period from 2000 to 2005 (L. Annemans, E Spaepen, M Gaskin, et al. Gout in the UK and Germany: prevalence, comorbidities, and management in general practice 2000-2005 [J]. Ann Rheum Dis, 2008, 67: 960-966). From an epidemiological study for 3978 urban persons aged 40 to 74, which was carried out in China in 2010, it was shown that 25% of investigated persons suffered from hyperuricemia (Raquel Villegas, Yong bing Xiang, Qiu yin Cai, et al. Prevalence and Determinants of Hyperuricemia in Middle-Aged, Urban Chinese Men [J]. Metabolic Syndrome and Related Disorders, 2010, 8(3):263-270); and the incidence thereof in inland regions was lower than that in coastal regions, while the incidence thereof in undeveloped areas was lower than that in developed areas (Hairong Nan, Qing Qiao, Yanhu Dong, et al. The prevalence of hyperuricemia in a population of the coastal city of Qingdao, China [J]. The Journal of Rheumatology, 2006, 33(7):1346-1350.). According to an analysis report from the Chinese Center for Diseases and Health Investigation in 2004, the number of hyperuricemia patients had then reached 0.12 billion in China, including more than 75 million gout patients, and in addition, the number was increasing at an annual growth rate of 0.97%, which seriously endangers people's life and health.

The occurrence of gout is caused by hyperuricemia due to constant increase of uric acid level in vivo. With supersaturation of uric acid level, sodium urate is crystallized and deposited in such sites as joints and soft tissues. When the uric acid level in vivo changes rapidly, and a partial wound leads to release of microcrystals or change of urate crystal protein coating, an inflammatory reaction of gout is caused, and then gout is induced. Uric acid is an end product of purine metabolism in nucleic acid (including nucleic acid in foods) in vivo. The content thereof is related with catabolism rate of nucleic acid in vivo and renal excretory function. When the generation of uric acid increases or excretion of uric acid reduces, it may both lead to deposition of uric acid and occurrence of hyperuricemia. It is generally believed that hyperuricemia occurs when the content of uric acid in serum is >420 μmol/L (70 mg/L) for male and >360 μmol/L (60 mg/L) for female at 37° C.

Gout may also cause many complications. According to statistics, for 90% gout patients, impotence, nephritis, calculus and the like will be induced, and complications such as chronic nephrosis and heart diseases may also be caused; for 50% patients, serious deformation of joints easily occurs and then causes disability; and for 30% patients, diseases such as uremia and renal failure are easily induced and then cause death (Grobner W, Walter-Sack I. Treatment of hyperuricemia and gout [J]. Med Monatsschr Pharm. 2005, 28(5): 159-164). Gout is also related with multiple diseases such as hypertension, metabolic syndrome, hyperlipidaemia, diabetes and insulin resistance (Terkeltaub R A. Clinical practice. Gout [J]. N Engl J Med. 2003, 349: 1647-1655) (Schlesinger N, Schumacher H R Jr. Gout: can management be improved ? [J]. Curr Opin Rheumatol. 2001, 13: 240-244).

Currently, medicines used for gout treatment mainly include anti-inflammatory agents, uricosuric drugs and uric acid production inhibitors.

Some anti-inflammatory agents such as colchicines, non-steroidal anti-inflammatory drugs (NSAIDS), adrenocorticotrophic hormone (ACTH), and glucocorticoid are mainly used for treatment of acute gouty arthritis, which can relieve patients from temporary pains. Colchicines is often accompanied by common adverse reactions such as diarrhea, emesis, and a spasm of abdominal pain; and non-steroidal anti-inflammatory drugs can relieve pains within a short period, but most of the non-steroidal anti-inflammatory drugs are accompanied by a serious gastrointestinal reaction. Adrenocorticotrophic hormone and glucocorticoid can inhibit infective inflammation, reduce hyperemia and edema, inhibit movement of inflammatory cells, and reduce individual immune level, which are used for treatment of severe acute gout patients accompanied with constitutional symptoms. However, such drugs have a strong rebound effect.

The uric acid level in vivo shall be reduced radically so as to better cure gout. The uric acid level in vivo is reduced mainly by two means of promoting uric acid excretion and reducing uric acid generation. Currently, drugs for promoting uric acid excretion in vivo mainly include probenecid, anturan, benzbromarone and the like. These drugs can inhibit reabsorption of uric acid by kidney tubules, and act on urate transporters of renal proximal tubules, thereby inhibiting reabsorption of uric acid, increasing excretion thereof, and consequently reducing the concentration of uric acid in vivo. Probenecid is developed by Merck Corp. (U.S.), with main side-effects of erythra, severe gastrointestinal stimulation, drug fever and the like. Benzbromarone (Narcaricin) developed by Sanofi-Synthelabo Ltd (France) and marketed since 1976, and anturan developed by Navatris Corp. (U.S.) and marketed since 1959, have the same action principle as probenecid. It was found through researches that due to main side-effects of such drugs, urine shall be alkalized when the drugs are administered to patients, and the drugs cannot be applied in patients with renal insufficiency. In addition, it was reported according to researches that benzbromarone has a very great hepatotoxicity, and so has been withdrawn from most of the European market (Jansen T L, Reinders M K, van Roon E N, et al. Benzbromarone with drawn from the European market: another case of "absence of evidence is evidence of absence"? [J]. Clin Exp Rheumatol, 2004, 22 (5):651).

Another type of drugs used for gout treatment are uric acid production inhibitors. Researches indicated that such drugs mainly inhibits transformation of purine to uric acid through inhibiting the activity of xanthine oxidase (XO) required in the procedure of purine metabolism, so as to radically reduce generation of uric acid, thereby taking effect of gout treatment. Allopurinol marketed in 1960s, as an analogue of hypoxanthine, is a competitive inhibitor of xanthine oxidase. Allopurinol is mainly applied in patients with renal insufficiency. Although allopurinol has been applied for half a century, patients are often accompanied with fever, allergic eruption, abdominal pain, diarrhea, and reduction of leukocytes and platelets, and it even has side-effects such as hepatic function damage. It was found through researches that oxipurinol, a metabolite of allopurinol, can also inhibit the activity of xanthine oxidase, but it was also found that toxic and side effects of allopurinol are also resulted from a metabolite thereof such as oxipurinol.

Febuxostat is a new generation of xanthine oxidase inhibitor, which is applied clinically in prevention and treatment of hyperuricemia and induced gout. Teijin (Japan) applied for marketing of febuxostat at the beginning of 2004, EU approved marketing thereof in May, 2008 and FDA (U.S.) approved marketing thereof in February 2009. Febuxostat can inhibit oxidation and reduction states of xanthine oxidase. By comparison, allopurinol has a weak capability of inhibiting oxidation state of xanthine oxidase. Febuxostat is metabolized mainly though hepar, while allopurinol is metabolized and excreted mainly through kidney, which can better avoid adverse effects of allopurinol caused by renal metabolism and excretion (Takano Y, Hase-Aoki K, Horiuchi H et al. Selectivity of febuxostat, a novel non-purine inhibitor of xanthine oxidase/xanthine dehydrogenase [J]. Life Sci. 2005, 76: 1835-1847) (Becker M A, schumacher H R Jr, Wortman R L. Febuxostat compared with allopurinol in patients with hyper-uricemia and gout [J]. N Engl J Med. 2005, 353: 2450-2461). According to a Phase III clinical test report, compared with a control group, the uric acid level of plasma in a treatment group is lower than 60 mg/L after completion of treatment. Patients sensitive to allopurinol can better adapt to febuxostat. Compared with a dosage of 300 mg/d allopurinol, a dosage of 80 mg/d to 120 mg/d febuxostat can more effectively reduce the urate level of plasma (Pohar S, Murphy G. Febuxostat for prevention of gout attacks [J]. Issues Emerg Health Technol. 2006, 87:1-4).

Xanthine oxidase inhibitors with a target spot of xanthine oxidase are all almost heterocyclic compounds till now, and are mostly nitrogen heterocyclic aromatic compounds, for example, phenyl pyrazole derivatives (WO9818765, JP10310578), 2-phenyl thiazole derivatives (WO9631211, JP2002105067), 3-phenyl isothiazole derivatives (JP6211815), C-fused pyridine derivatives (WO2005121153), 2-phenyl thiophene derivatives (WO2006022375), 2-phenyl pyridine derivatives (WO2006022374), aryltriazole compounds (Nakazawa T, Miyata K, Omura K, et al. Metabolic profile of FYX-051 (4-(5-pyridin-4-yl-1H-[1,2,4]triazol-3-yl)pyridine-2-carbo- nitrile) in the rat, dog, monkey, and human: identification of N-glucuronides and N-glucosides [J]. Drug Metab Dispos, 2006, 34(11): 1880-1886), triaryl formic acid derivatives (WO2007043457), and the like as reported. Because such drugs can radically reduce generation of uric acid and take effect of gout treatment, great importance is attached to development of the drugs. With further research on a target spot of xanthine oxidase, and constant development of computers and the like, crystal structure of xanthine oxidase is completely analyzed, so as to further identify function mechanism of the drugs, thereby establishing a necessary basis for research on these drugs.

In last decades, the development of xanthine oxidase inhibitors was slow, which is related with a small proportion of hyperuricemia and gout patients. However, the incidence of hyperuricemia and gout showed an increasing tendency in recent years, which attracted great attention of researchers on anti-gout drug studies. Meanwhile, with further research on xanthine oxidase and reductase, it was found that inhibition of the activity of xanthine oxidase and reductase can contribute to treatment of hyperuricemia, and has a certain treatment effect of ischemia/ischemia-reperfusion injury and especially heart failure, which indicates that a xanthine oxidase inhibitor with high efficiency and low toxicity has huge development potentials and application values. With respect to the chronic and stubborn disease of gout, design of new drugs with an action target of xanthine oxidase has attracted great attention widely. Multiple compounds with high activity have gone through clinical tests. However, there are many problems faced such as great toxic and side effects, which need to be researched more deeply.

SUMMARY

An objective of the present invention is to provide a 2-aryl selenazole compound based on the prior art.

Another objective of the present invention is to provide application of the 2-aryl selenazole compound in terms of preparing a xanthine oxidase inhibitor, or preparing a drug used for prevention or treatment of hyperuricemia, gout, diabetic nephropathy, an inflammatory disease, a neurological disease and the like.

The objectives of the present invention can be achieved by the following measures:

A 2-aryl selenazole compound represented by formula (I) or a pharmaceutically acceptable salt thereof is provided,

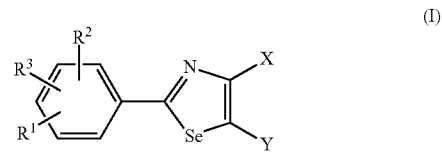

where,
X is selected from $C_{1-2}$ alkyl or substituted $C_{1-2}$ alkyl;
Y is selected from —COOR$^a$ or —CONHR$^a$;
R$^1$ is selected from halogen, —CN, $C_{1-2}$ alkyl, substituted $C_{1-2}$ alkyl, $C_{1-3}$ alkoxy, or substituted $C_{1-3}$ alkoxy;
R$^2$ is selected from H, D, halogen, $C_{1-2}$ alkyl, substituted $C_{1-2}$ alkyl, $C_{1-3}$ alkoxy, or substituted $C_{1-3}$ alkoxy; and
R$^3$ is selected from —(CH$_2$)$_n$—O—R$^b$, —(CH$_2$)$_n$—S—R$^b$, —C(O)R$^b$, —NR$^c$R$^d$, —S(O)CHR$^c$R$^d$, —S(O)$_2$CHR$^c$R$^d$, —(CH$_2$)$_n$C(O)NR$^c$R$^d$, aryl, substituted aryl, a heterocyclic radical, a substituted heterocyclic radical, a heteroaryl radical, or a substituted heteroaryl radical, where, n is 0 to 2;

$R^a$ is selected from H, $C_{1-6}$ alkyl or substituted $C_{1-6}$ alkyl;

$R^b$ is selected from H, $C_{1-8}$ alkyl, substituted $C_{1-8}$ alkyl, aryl, substituted aryl, a heterocyclic radical, a substituted heterocyclic radical, a heteroaryl radical, or a substituted heteroaryl radical; and $R^c$ and $R^d$ are respectively independently selected from H, $C_{1-8}$ alkyl, or substituted $C_{1-8}$ alkyl; or $R^c$ and $R^d$ are cyclized to form a cycloalkyl, a substituted cycloalkyl, a heteroaryl radical, or a substituted heteroaryl radical; and A substituent in groups X, Y, $R^1$, $R^2$, $R^3$, $R^a$, $R^b$, $R^c$ or $R^d$ is selected from one or more of D, —OH, —CN, —NH$_2$, acyl, acylamino, halogen, $C_{1-4}$ alkyl, halogenated $C_{1-4}$ alkyl, deuterated $C_{1-4}$ alkyl, $C_{1-2}$ alkoxy, or $C_{1-2}$ aminoalkyl.

In a preferred solution, the 2-aryl selenazole compound of the present invention may further be a compound with the structure of formula (II) or a pharmaceutically acceptable salt thereof.

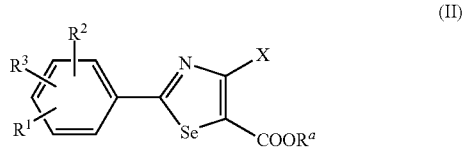

(II)

In a preferred solution, X is $C_{1-3}$ alkyl, or halogenated or hydroxy-substituted $C_{1-3}$ alkyl.

Further, X is —CH$_3$, —CH$_2$CH$_3$, —CH$_2$OH or —CF$_3$.

Further, X is —CH$_3$.

In a preferred solution, Y is —COOR$^a$, and R$^a$ is H, $C_{1-3}$ alkyl, or substituted $C_{1-3}$ alkyl.

Further, Y is —COOH.

In a preferred solution, $R^1$ is selected from halogen, —CN, $C_{1-2}$ alkyl, halogenated $C_{1-2}$ alkyl, $C_{1-2}$ alkoxy, or halogenated $C_{1-2}$ alkoxy.

Further, $R^1$ is selected from halogen, —CN, —CH$_3$, —CH$_2$CH$_3$, —CHF$_2$, —CF$_3$, —OCHF$_2$, or —OCF$_3$.

Further, $R^1$ is selected from Cl, Br, —CN, or —CF$_3$.

In a preferred solution, $R^2$ is selected from H or D.

In a preferred solution, the compound of the present invention may be a compound represented by formula (III) or a pharmaceutically acceptable salt thereof.

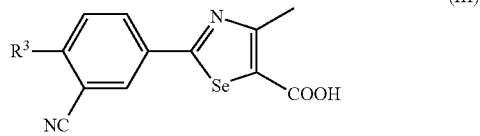

(III)

In a preferred solution, $R^3$ is selected from —OR$^b$, —SR$^b$, —C(O)R$^b$, —NR$^c$R$^d$, —S(O)CHR$^c$R$^d$, —S(O)$_2$CHR$^c$R$^d$, —C(O)NR$^c$R$^d$, phenyl, substituted phenyl, pyridyl, substituted pyridyl, naphthyl, substituted naphthyl, phenoxy, substituted phenoxy, thiophenyl, substituted thiophenyl, morpholinyl, substituted morpholinyl, N-ethyl morpholinyl, substituted N-ethyl morpholinyl, piperazinyl, substituted piperazinyl, 4,5,6,7-tetrahydrothieno[3,2-c]pyridyl, methylphenyl sulfonyl, or substituted methylphenyl sulfonyl.

Further, $R^3$ is selected from —OR$^b$, —SR$^b$, —C(O)R$^b$, —NR$^c$R$^d$, —S(O)$_2$CHR$^c$R$^d$, —C(O)NR$^c$R$^d$, phenyl, substituted phenyl, pyridyl, substituted pyridyl, naphthyl, substituted naphthyl, quinolyl, substituted quinolyl, thiophenyl, substituted thiophenyl, phenoxy, substituted phenoxy, pyridylthio, morpholinyl, piperazinyl, substituted piperazinyl, or 4,5,6,7-tetrahydrothieno[3,2-c]pyridyl.

In a preferred solution, $R^b$ is $C_{1-8}$ alkyl, substituted $C_{1-8}$ alkyl, phenyl or substituted phenyl; $R^c$ or $R^d$ is independently selected from H, $C_{1-8}$ alkyl, or substituted $C_{1-8}$ alkyl; or $R^c$ and $R^d$ are cyclized to form cycloalkyl, substituted cycloalkyl, a heteroaryl radical, or a substituted heteroaryl radical.

In a preferred solution, the substituent is selected from one or more of D, —OH, —NH$_2$, —CN, acyl, halogen, $C_{1-4}$ alkyl, halogenated $C_{1-4}$ alkyl, deuterated $C_{1-4}$ alkyl, or $C_{1-2}$ alkoxy.

Further, the substituent is selected from one or more of D, —OH, —NH$_2$, —CN, —NHCH$_3$, —F, —Cl, —Br, —CH$_3$, —CH$_2$CH$_3$, —CHDCH$_2$D, —CF$_3$, —OCH$_3$, or —OCH$_2$CH$_3$.

In another preferred solution, $R^3$ is selected from —OCH$_2$CH$_3$, —OCH(CH$_3$)$_2$, —OCH$_2$CH(CH$_3$)$_2$, —OCH$_2$CH$_2$CH(CH$_3$)$_2$, —OCH$_2$C$_6$H$_{11}$, —OCH$_2$C$_3$H$_5$, —SCH(CH$_3$)$_2$, —SCH$_2$CH(CH$_3$)$_2$, —S(O)$_2$CH(CH$_3$)$_2$, —CH$_2$SCH(CH$_3$)$_2$, —N(CH$_3$)$_2$, phenyl, methoxyphenyl, dimethoxyphenyl, trimethoxyphenyl, methoxyfluorophenyl, trifluoromethoxyphenyl, chlorophenyl, difluorophenyl, pentadeuterophenyl, methylpiperazinylphenyl, aniline formyl, benzylthio, benzyloxy, naphthyl, pyridyl, pyridylthiophenyl, dideuteroethylpyridyl, thiophenyl, chlorothiophenyl, (trifluoromethyl)phenyl, (trifluoromethylthio)phenyl, morpholinyl, methylpiperazinyl, or 4,5,6,7-tetrahydrothieno[3,2-c]pyridyl.

The 2-aryl selenazole compound of the present invention may further be selected from the following compounds or pharmaceutically acceptable salts thereof:

2-(3-cyano-4-ethoxyphenyl)-4-methyl-selenazole-5-carboxylic acid, 2-(3-cyano-4-isobutoxyphenyl)-4-methyl-selenazole-5-carboxylic acid, 2-(3-cyano-4-isopropoxyphenyl)-4-methyl-selenazole-5-carboxylic acid, 2-[3-cyano-4-(3-methyl-butoxy)phenyl]-4-methyl-selenazole-5-carboxylic acid, 2-[3-cyano-4-(cyclohexylmethoxy)phenyl]-4-methyl-selenazole-5-carboxylic acid, 2-[3-cyano-4-(benzyloxy)phenyl]-4-methyl-selenazole-5-carboxylic acid, 2-[3-cyano-4-(cyclopropylmethoxy)phenyl]-4-methyl-selenazole-5-carboxylic acid, 2-(2-cyano-biphenyl-4-yl)-4-methyl-selenazole-5-carboxylic acid, 2-(2-cyano-3',4'-dimethoxybiphenyl-4-yl)-4-methyl-selenazole-5-carboxylic acid, 2-(2-cyano-3'-fluoro-4'-methoxybiphenyl-4-yl)-4-methyl-selenazole-5-carboxylic acid, 2-(2-cyano-3',4',5'-trimethoxybiphenyl-4-yl)-4-methyl-selenazole-5-carboxylic acid, 2-(2-cyano-4'-methoxybiphenyl-4-yl)-4-methyl-selenazole-5-carboxylic acid, 2-(2-cyano-3'-methoxybiphenyl-4-yl)-4-methyl-selenazole-5-carboxylic acid, 2-(2-cyano-3'-trifluoromethoxybiphenyl-4-yl)-4-methyl-selenazole-5-carboxylic acid, 2-(2-cyano-4'-chlorobiphenyl-4-yl)-4-methyl-selenazole-5-carboxylic acid, 2-(2-cyano-3',4'-difluorobiphenyl-4-yl)-4-methyl-selenazole-5-carboxylic acid, 2-(2-cyano-2',3',4',5',6'-pentadeuterobiphenyl-4-yl)-4-methyl-selenazole-5-carboxylic acid,
2-(2-cyano-2'-methoxybiphenyl-4-yl)-4-methyl-selenazole-5-carboxylic acid,
2-(2-cyano-2',4'-dimethoxybiphenyl-4-yl)-4-methyl-selenazole-5-carboxylic acid,
2-[3-cyano-4-(1-naphthyl)-phenyl]-4-methyl-selenazole-5-carboxylic acid,
2-[3-cyano-4-(4-pyridyl)-phenyl-4-yl]-4-methyl-selenazole-5-carboxylic acid,
2-[3-cyano-4-(3-pyridyl)-phenyl-4-yl]-4-methyl-selenazole-5-carboxylic acid,
2-[2-cyano-4'-(1,2-deuteroethyl)-biphenyl-4-yl]-4-methyl-selenazole-5-carboxylic acid,
2-(2-cyano-6-deuterobiphenyl-4-yl)-4-methyl-selenazole-5-carboxylic acid,
2-(3-cyano-4-isopropylthiophenyl)-4-methyl-selenazole-5-carboxylic acid,
2-(3-cyano-4-isobutylthiophenyl)-4-methyl-selenazole-5-carboxylic acid,
2-[3-cyano-4-(4-chrolophenylthio)-phenyl]-4-methyl-selenazole-5-carboxylic acid,
2-[3-cyano-4-(3-trifluoromethylthiophenyl)-phenyl]-4-methyl-selenazole-5-carboxylic acid,
2-[3-cyano-4-(2-pyridylthio)-phenyl]-4-methyl-selenazole-5-carboxylic acid,
2-(3-cyano-4-benzylthio-phenyl)-4-methyl-selenazole-5-carboxylic acid,
2-(3-cyano-4-isopropyl sulfone-phenyl)-4-methyl-selenazole-5-carboxylic acid,
2-(3-cyano-4-morpholinyl-4-yl-phenyl)-4-methyl-selenazole-5-carboxylic acid,
2-[3-cyano-4-(4-methylpiperazine-1-yl)phenyl]-4-methyl-selenazole-5-carboxylic acid,
2-{3-cyano-4-(6,7-dihydro-4H-thieno[3,2-c]pyridyl)-phenyl}-4-methyl-selenazole-5-carboxylic acid, 2-(3-cyano-4-dimethylamino-phenyl)-4-methyl-selenazole-5-carboxylic acid,
2-(3-chloro-4-isobutoxyphenyl)-4-methyl-selenazole-5-carboxylic acid,
2-(3-trifluoromethyl-4-isobutoxyphenyl)-4-methyl-selenazole-5-carboxylic acid,
2-[3-cyano-4-(isopropylthiomethyl)-phenyl]-4-methyl-selenazole-5-carboxylic acid,
2-[3-bromo-4-(aniline formyl)-phenyl]-4-methyl-selenazole-5-carboxylic acid,
2-(2-cyano-4'-trifluoromethylbiphenyl-4-yl)-4-methyl-selenazole-5-carboxylic acid,
2-(2-cyano-3'-trifluoromethylbiphenyl-4-yl)-4-methyl-selenazole-5-carboxylic acid,
2-(2-cyano-2'-trifluoromethylbiphenyl-4-yl)-4-methyl-selenazole-5-carboxylic acid,
2-(3-cyano-4-isobutoxyphenyl)-4-hydroxymethyl-selenazole-5-carboxylic acid,
2-(3-bromo-4-isobutoxyphenyl)-4-methyl-selenazole-5-carboxylic acid,
2-(3-cyano-4-isopropylthiophenyl)-4-methyl-selenazole-5-carboxylic acid-(2-N-acetyl)ethyl ester,
2-(3-cyano-4-tertbutylthiophenyl)-4-methyl-selenazole-5-carboxylic acid,
2-(3-cyano-4-cyclohexylthiophenyl)-4-methyl-selenazole-5-carboxylic acid,
2-(3-trifluoromethylphenyl)-4-methyl-selenazole-5-carboxylic acid.

A compound of the present invention, 2-(3-cyano-4-isopropylthiophenyl)-4-methyl-selenazole-5-carboxylic acid-(2-N-acetyl)ethyl ester may be a prodrug of 2-(3-cyano-4-isopropylthiophenyl)-4-methyl-selenazole-5-carboxylic acid.

The compound of the present invention has the following synthesis routes:

Synthesis Route 1:

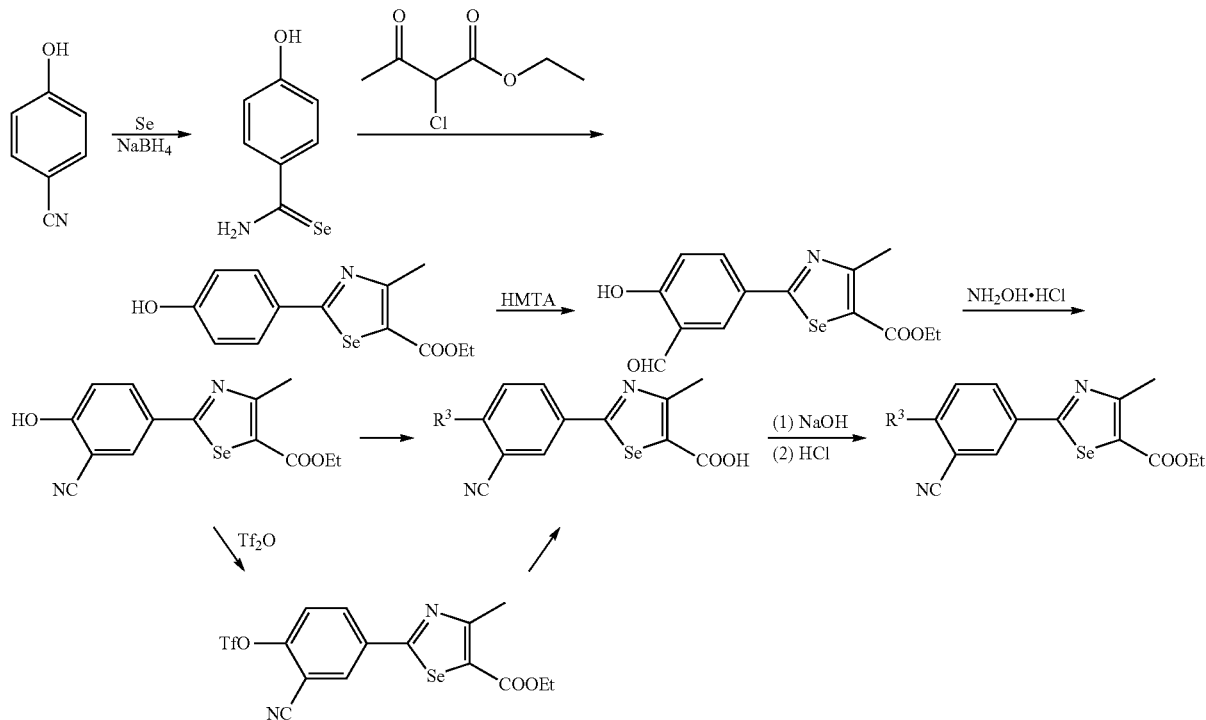

Synthesis Route 2:

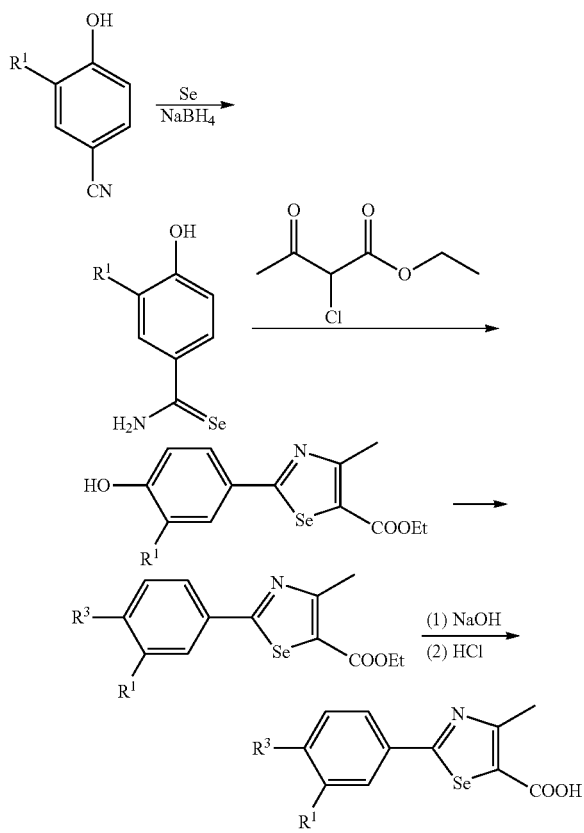

The compound of the present invention may be prepared by using the foregoing methods or similar methods, and corresponding raw materials are selected according to different substituents and different positions of a substituent. Special preparation methods will be described in detail with reference to embodiments.

Unless otherwise stated, the following terms as used in the claims and specification are defined below:

"Hydrogen" refers to protium (1H), a primary stable isotope of hydrogen element.

"Deuterium" refers to a stable form of hydrogen, also called heavy hydrogen, with an element symbol of D.

"Alkyl" refers to a saturated aliphatic alkyl group having 1 to 20 carbon atoms, including a straight chain and a branched chain group (a numerical range mentioned herein, for example, "1 to 20", indicates that the group (an alkyl group here) may contain 1 carbon atom, 2 carbon atoms, 3 carbon atoms, and so forth, till 20 carbon atoms). An alkyl group containing 1 to 4 carbon atoms is called lower alkyl. When a lower alkyl has no substituent, it is called unsubstituted lower alkyl. More preferably, the alkyl is an alkyl group of a moderate size having 1 to 10 carbon atoms, for example, methyl, ethyl, propyl, 2-propyl, butyl, isobutyl, tertiary butyl, amyl, and the like. Most preferably, the alkyl is a lower alkyl group having 1 to 4 carbon atoms, for example, methyl, ethyl, propyl, 2-propyl, butyl, isobutyl, tertiary butyl, or the like. The alkyl may be substituted or unsubstituted.

"Cycloalkyl" in the present invention refers to a group of an all-carbon single or fused ring (the "fused" ring means that each ring in a system shares an adjacent pair of carbon atoms with another ring in the system), where one or more rings have no fully-connected π electron system, and the group generally has 3 to 10 carbon atoms. Embodiments of the cycloalkyl include (but are not limited to) cyclopropane, cyclobutane, cyclopentane, cyclopentene, cyclohexane, adamantane, cyclohexadiene, cycloheptane and cycloheptatriene. The cycloalkyl may be substituted or unsubstituted.

"Heterocyclic radical" in the present invention includes "heterocyclic alkyl" and "heterocyclic aryl". The "heterocyclic alkyl" refers to a group of a single ring or saturated fused ring containing at least one heteroatom (the "fused" ring means that each ring in a system shares an adjacent pair of carbon atoms with another ring in the system), where one or more rings have no fully-connected π electron system, and the group generally has 3 to 10 carbon atoms. The "heterocyclic aryl" in the present invention refers to a group of a single or fused ring having 5 to 12 annular atoms, which contains 1, 2, 3 or 4 heterocyclic atoms selected from N, O or S in addition to other carbon atoms, and also has a fully conjugated π electron system. Embodiments of unsubstituted heterocyclic aryl include but are not limited to pyrrole, furan, thiophene, imidazole, oxazole, thiazole, pyrazole, pyridine, quinoline, isoquinoline, purine, tetrazole, triazine and carbazole. The heterocyclic aryl may be substituted or unsubstituted.

"Aryl" in the present invention refers to a group of an all-carbon single ring or a polycyclic fused ring containing 6 to 12 carbon atoms, which has a fully conjugated it electron system. Embodiments of the aryl include but are not limited to phenyl, naphthyl and naphthyl. The alkyl may be substituted or unsubstituted.

"Hydroxyl" refers to a —OH group.

"Alkoxy" refers to a —O-(unsubstituted alkyl) group and a —O-(unsubstituted cycloalkyl) group, and further represents a —O-(unsubstituted alkyl) group. Typical embodiments thereof include but are not limited to methoxyl, ethoxyl, propoxyl, butoxyl, cyclopropoxyl, cyclobutoxyl, cyclopentyloxy, cyclohexyloxyl, and the like.

"Phenyl" refers to a group of a benzene ring

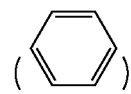

with any position thereon connected with another group.

"Thiophenyl" refers to a —S-phenyl group.

"Phenoxyl" refers to a —O-phenyl group.

"Alkylcarbonyl" refers to a group of (unsubstituted alkyl)-C(=O)— and a group of (unsubstituted cycloalkyl)-C(=O)—, and further refers to the former.

"Halogen" refers to fluorine, chlorine, bromine or iodine, and is preferably fluorine, chlorine, or bromine.

"Cyano" refers to a —CN group.

"Nitryl" refers to a —$NO_2$ group.

"Acyl" refers to a —C(O)Q group, where Q may be hydrogen (then the acyl formed is formyl), and may also be alkyl, aminoalkyl, aryl and aminoaryl, for example, acetyl, propionyl, phenylcarbamoyl, benzoyl, and the like.

"Amino" refers to a —$NH_2$ group.

"Aminoalkyl" refers to a —NH-alkyl group.

"Deuterated alkyl" refers to a group where one or more hydrogen atoms of an alkyl group are substituted by deuterium atoms.

"Naphthyl" refers to a group of a naphthalene ring

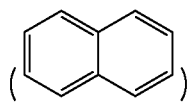

with any position thereon connected with another group.

"Pyridyl" refers to a group of a pyridine ring

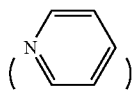

with any one of positions 2 to 6 thereon connected with another group.

"Thiopyridyl" refers to a —S-pyridyl group.

"Morpholinyl" refers to a group of a morpholine ring

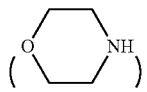

with any one (including N—) of positions 2 to 6 thereon connected with another group.

"Piperazinyl" refers to a group of a piperazine ring

with any position (including N—) thereon connected with another group.

"Methylphenyl sulfonyl" refers to a group of methyl phenyl sulfone

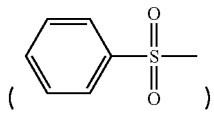

with $CH_3$—thereon connected with another group.

"4,5,6,7-Tetrahydrothieno[3,2-c]pyridyl" refers to a group of 4,5,6,7-tetrahydrothieno[3,2-c]pyridine ring

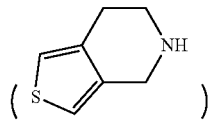

with any one (including N—) of positions available for connection with another group being connected with another group.

"$C_{3-8}$" and "$C_{1-8}$" in a group of "$C_{1-8}$ alkoxy substituted by $C_{3-8}$ cycloalkyl" in the present invention only restricts the number of carbon atoms of an adjacent group thereof, rather than the number of carbon atoms of the whole group.

"Pharmaceutically acceptable salt" refers to a salt formed by a compound of formula (I) or (II) and an organic or inorganic acid, representing salts that maintain the bio-availability and properties of a parent compound. The salts include:

(1) a salt formed by reaction with an acid, that is, obtained from reaction of free alkali of a patent compound and an inorganic or organic acid, where the inorganic acid includes (but is not limited to) hydrochloric acid, hydrobromic acid, nitric acid, phosphoric acid, metaphosphoric acid, sulfuric acid, sulphurous acid, and perchloric acid; and the organic acid includes (but is not limited to) acetic acid, propionic acid, acrylic acid, oxalic acid, D- or L-malic acid, fumaric acid, maleic acid, hydroxybenzoic acid, γ-hydroxybutyric acid, methoxybenzoic acid, phthalic acid, methanesulfonic acid, ethanesulfonic acid, naphthalene-1-sulfonic acid, naphthalene-2-sulfonic acid, p-toluenesulfonic acid, salicylic acid, tartaric acid, citric acid, lactic acid, mandelic acid, succinic acid, or malonic acid.

(2) a salt generated by an acidic proton present in a parent compound being substituted by a metal ion, or coordinated with an organic alkali, where the metal ion is, for example, an alkali metal ion, an alkaline-earth metal ion, or an aluminum ion; and the organic alkali is, for example, ethanol amine, diethanol amine, triethanol amine, trometamol, N-methyloctanamide, or the like.

"Pharmaceutical composition" refers to one or more compounds described herein or a pharmaceutically acceptable salt thereof, a prodrug, and another chemical composition, for example, a mixture of a pharmaceutically acceptable carrier and excipient. The pharmaceutical composition is used to promote administration of a compound to an organism.

"Prodrug" refers to a compound that takes a pharmacological effect only after being transformed in vivo. The prodrug itself has no or low bioactivity, and is transformed to an active substance through metabolism in vivo. This process aims to increase the bio-availability of drugs, enhance targeting, and reduce the toxicity and side effects of drugs.

The present invention provides a pharmaceutical composition, including any compound or pharmaceutically acceptable salt thereof in the present invention as an active ingredient.

The compound of the present invention or a pharmaceutically acceptable salt thereof can be applied in terms of preparing a xanthine oxidase inhibitor drug.

The compound of the present invention or a pharmaceutically acceptable salt thereof can be applied in terms of preparing a drug used for prevention or treatment of hyperuricemia, gout, diabetic nephropathy, an inflammatory disease or a neurological disease.

BRIEF DESCRIPTION OF THE DRAWINGS

DETAILED DESCRIPTION

The following preparation examples and embodiments are provided so that a person skilled in the art can more clearly understand and implement the present invention. They shall not be construed as a limitation on the scope of the present invention, but are merely used for illustration and representation thereof.

SYNTHESIS EMBODIMENTS

Embodiment 1

Synthesis of 2-(3-cyano-4-ethoxyphenyl)-4-methyl-selenazole-5-carboxylic acid (6)

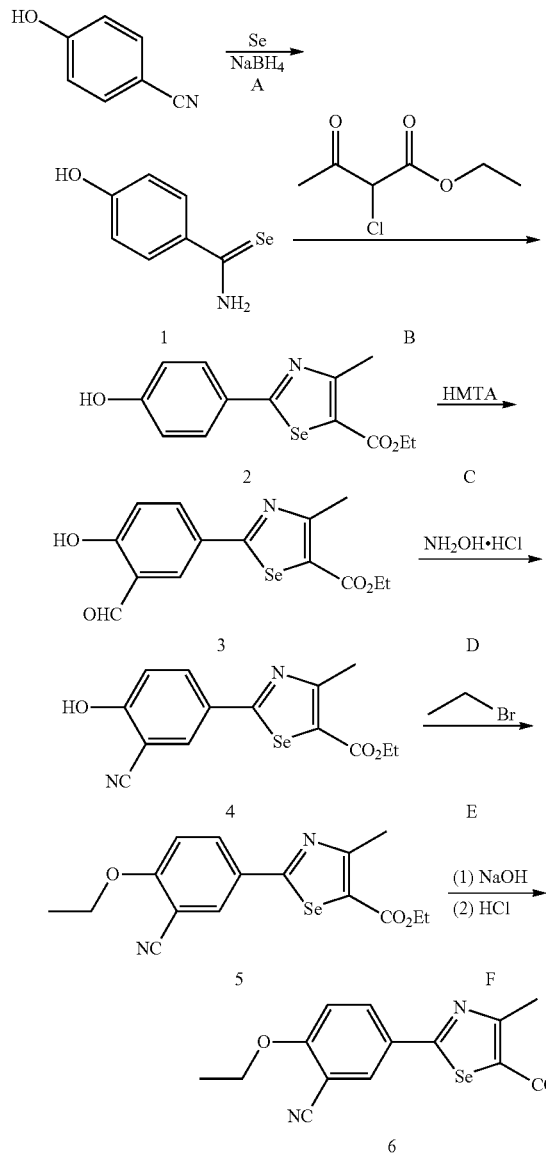

Step A: Anhydrous ethanol (540 mL) was added dropwise into a mixture of selenium powder (50.0 g, 0.633 mol) and sodium borohydride (26.4 g, 0.698 mol) within 3 h to 4 h under the protection of nitrogen in an ice-water bath, then heated to room temperature, and stirred for 1 h. The mixture was then added with pyridine solution (126 mL) containing 4-cyanophenol (18.84 g, 0.158 mol), and heated until reflux occurred. After 2M hydrochloric acid solution (320 mL) was added dropwise slowly for no less than 4 h, the resulting solution was stirred overnight under reflux. A TLC analysis indicated that the reaction was completed. The solution was distilled under reduced pressure to remove most of ethanol, added with water (400 mL) for dilution, and extracted with ethyl acetate (200 mL×2). The combined organic phase was washed with 2M hydrochloric acid (100 mL), and then washed with saturated saline solution (100 mL). After the solvent was removed by means of reduced pressure distillation, the resulting product was recrystallized with petroleum ether/ethyl acetate, to obtain p-hydroxy-seleno-benzamide (1) (25.0 g), with a yield of 79.1%.

Step B: The compound 1 (25.0 g, 0.125 mol) and ethyl 2-chloroacetoacetate (24.7 g, 0.150 mol) were added into anhydrous ethanol (500 mL), heated, and stirred under reflux for 3 h. A TLC analysis indicated that the reaction was completed. The reaction solution was cooled to room temperature. After suction filtration under reduced pressure, the filter cake was collected and dried, to obtain 2-(4-hydroxyphenyl)-4-methyl-selenazole-5-ethyl formate (2) (32.7 g), with a yield of 84.3%.

$^1$H NMR (DMSO-$d_6$, 400 MHz) δ 7.81 (dd, J=2.0, 6.8 Hz, 2H), 6.87 (dd, J=2.0, 6.8 Hz, 2H), 4.26 (q, J=6.8 Hz, 2H), 2.64 (s, 3H), 1.28 (t, J=6.8 Hz, 3H).

Step C: The compound 2 (17.6 g, 56.7 mmol) and hexamethylene tetramine (HMTA) (9.8 g, 69.9 mmol) were added into trifluoroacetic acid (85 mL). The reaction solution was heated to 85° C. and stirred for 42 h. A TLC analysis indicated that the reaction was completed. The solution was distilled under reduced pressure to remove most of the solvent, then added with water (300 mL), stirred for 60 min and filtered. The filter cake was dissolved in ethyl acetate (200 mL), separated from residual water, and dried with anhydrous sodium sulfate. After the solvent was removed by means of reduced pressure distillation, the resulting product was separated and purified by using a silica column (200 to 300 mesh silica gel, ethyl acetate/petroleum ether=1/8 for elution), so as to obtain 2-(3-formyl-4-hydroxyphenyl)-4-methyl-selenazole-5-ethyl formate (3) (8.7 g), with a yield of 45.3%.

Step D: The compound 3 (8.7 g, 25.7 mmol), hydroxylamine hydrochloride (2.6 g, 37.4 mmol) and sodium formate (2.5 g, 36.7 mmol) were added into formic acid (90 mL), and the resulting solution was heated and stirred under reflux for 42 h. A TLC analysis indicated that the reaction was completed. The reaction solution was cooled to room temperature and added with water (270 mL) to separate out abundant solids, and was then further cooled to 0-5° C., stirred for 30 min and filtered. The filter cake was washed with abundant water and vacuum-dried to obtain a light yellow solid. The solid was recrystalized with petroleum ether/ethyl acetate, to obtain 2-(3-cyano-4-hydroxyphenyl)-4-methyl-selenazole-5-ethyl formate (4) (7.0 g), with a yield of 81.2%.

Step E: The compound 4 (70 mg, 0.209 mmol) was dissolved in DMF (5 mL), and added with potassium iodide (7 mg, 0.042 mmol), anhydrous potassium carbonate (34.7 mg, 0.251 mmol) and ethyl bromide (32 mg, 0.293 mmol). The resulting mixture was stirred overnight at 70° C. The mixture was cooled to room temperature, added with water for dilution, and then filtered. The filter cake was purified by using a silica column (200 to 300 mesh silica gel, ethyl acetate/petroleum ether=1/20 for elution), so as to obtain a product, 2-(3-cyano-4-ethyoxyphenyl)-4-methyl-selenazole-5-ethyl formate (5), which was directly used for the next step reaction.

Step F: The compound 5 obtained from the last step reaction was dissolved in THF (4 mL) and methanol (11 mL), and added with 2M sodium hydroxide solution (3 mL). The resulting mixture was heated to 55° C. and stirred for 0.5 h. After the reaction was completed, about half of the solvent was removed by means of reduced pressure distillation. The solution was added with water (20 mL) and then with diluted hydrochloric acid so as to adjust the pH value to 5-6, filtered and dried to obtain 2-(3-cyano-4-ethyoxyphenyl)-4-methyl-selenazole-5-carboxylic acid (6).

$^1$H NMR (DMSO-$d_6$, 400 MHz) δ 8.23 (s, 1H), 8.17 (d, J=8.4 Hz, 1H), 7.32 (d, J=8.4 Hz, 1H), 4.27 (q, J=6.8 Hz, 2H), 2.67 (s, 3H), 1.39 (t, J=6.4 Hz, 3H). MS (EI, m/z): 335.1 [M−H]$^-$.

Embodiment 2

Synthesis of 2-(3-cyano-4-isobutoxyphenyl)-4-methyl-selenazole-5-carboxylic acid (7)

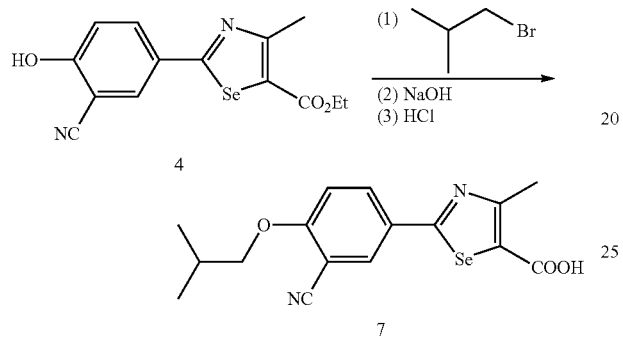

The compound 4 was reacted with 1-bromo-2-methylpropane according to step E in Embodiment 1, then hydrolyzed according to step F in Embodiment 1, and acidized to obtain 2-(3-cyano-4-isobutoxyphenyl)-4-methyl-selenazole-5-carboxylic acid (7).

$^1$H NMR (DMSO-$d_6$, 400 MHz) δ 8.26 (d, J=2.4 Hz, 1H), 8.18 (dd, J=2.0, 9.2 Hz, 1H), 7.34 (d, J=9.2 Hz, 1H), 4.00 (d, J=6.8 Hz, 2H), 2.63 (s, 3H), 2.14-2.04 (m, 1H), 1.02 (d, J=6.8 Hz, 6H). MS (EI, m/z): 363.2 [M−H]$^-$.

Embodiment 3

Synthesis of 2-(3-cyano-4-isopropoxyphenyl)-4-methyl-selenazole-5-carboxylic acid (8)

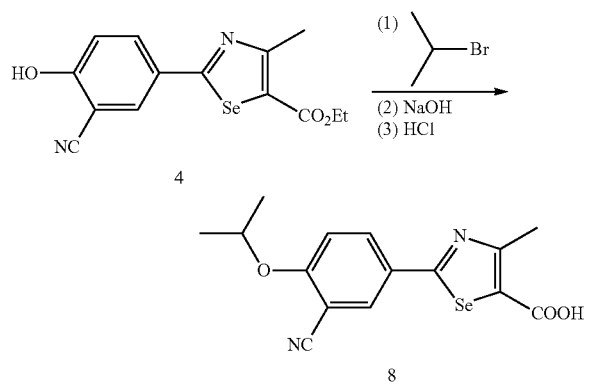

The compound 4 was reacted with isopropyl bromide according to step E in Embodiment 1, then hydrolyzed according to step F in Embodiment 1, and acidized to obtain 2-(3-cyano-4-isopropoxyphenyl)-4-methyl-selenazole-5-carboxylic acid (8).

$^1$H NMR (DMSO-$d_6$, 400 MHz) δ 8.29 (d, J=2.4 Hz, 1H), 8.20 (dd, J=2.4, 8.8 Hz, 1H), 7.38 (d, J=8.8 Hz, 1H), 4.94-4.88 (m, 1H), 2.65 (s, 3H), 1.36 (d, J=6.0 Hz, 6H). MS (EI, m/z): 349.1 [M−H]$^-$.

Embodiment 4

Synthesis of 2-[3-cyano-4-(3-methyl-butoxy)phenyl]-4-methyl-selenazole-5-carboxylic acid (9)

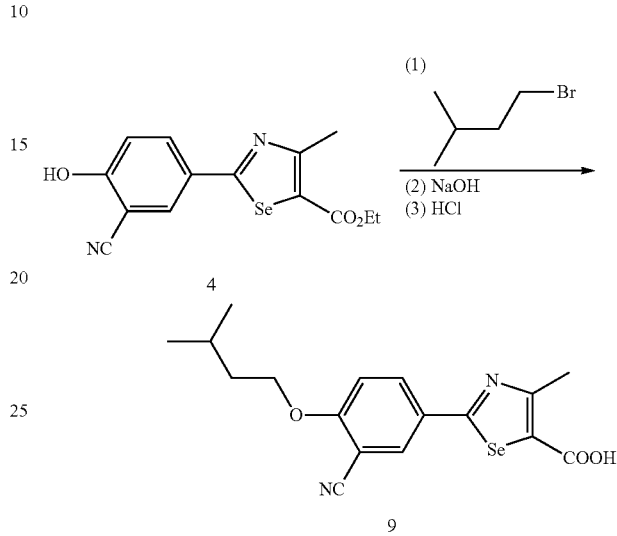

The compound 4 was reacted with 3-methyl-1-bromobutane according to step E in Embodiment 1, then hydrolyzed according to step F in Embodiment 1, and acidized to obtain 2-[3-cyano-4-(3-methyl-butoxy)phenyl]-4-methyl-selenazole-5-carboxylic acid (9).

$^1$H NMR (DMSO-$d_6$, 400 MHz) δ 13.28 (s, 1H), 8.30 (d, J=1.6 Hz, 1H), 8.22 (dd, J=1.6, 8.8 Hz, 1H), 7.38 (d, J=8.8 Hz, 1H), 4.26-4.25 (m, 2H), 2.65 (s, 3H), 1.86-1.78 (m, 1H), 1.70-1.68 (m, 2H), 0.96 (d, J=6.8 Hz, 6H). MS (EI, m/z): 377.2 [M−H]$^-$.

Embodiment 5

Synthesis of 2-[3-cyano-4-(cyclohexylmethoxy)phenyl]-4-methyl-selenazole-5-carboxylic acid (10)

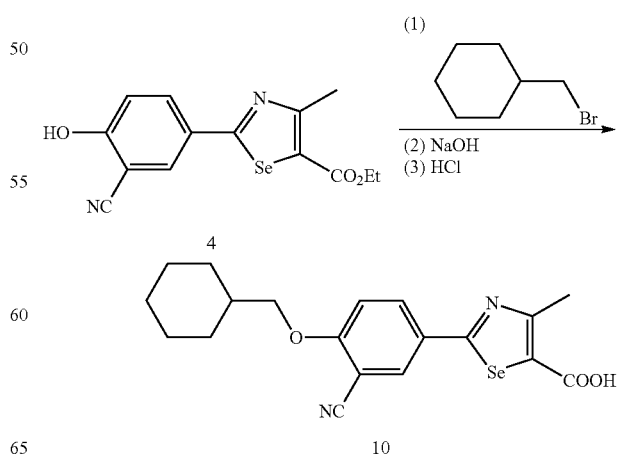

The compound 4 was reacted with cyclohexylmethyl bromide according to step E in Embodiment 1, then hydrolyzed according to step F in Embodiment 1, and acidized to obtain 2-[3-cyano-4-(cyclohexylmethoxy)phenyl]-4-methyl-selenazole-5-carboxylic acid (10).

$^1$H NMR (DMSO-$d_6$, 400 MHz) δ 8.18 (d, J=2.4 Hz, 1H), 8.12 (dd, J=2.0, 8.8 Hz, 1H), 7.32 (d, J=8.8 Hz, 1H), 4.01 (d, J=6.0 Hz, 2H), 2.64 (s, 3H), 1.91-1.65 (m, 5H), 1.29-1.07 (m, 6H). MS (EI, m/z): 403.2 [M−H]$^-$.

Embodiment 6

Synthesis of 2-[3-cyano-4-(benzyloxy)phenyl]-4-methyl-selenazole-5-carboxylic acid (11)

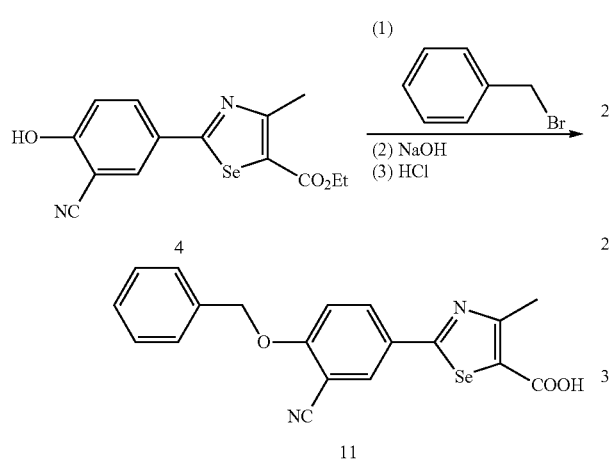

The compound 4 was reacted with benzyl bromide according to step E in Embodiment 1, then hydrolyzed according to step F in Embodiment 1, and acidized to obtain 2-[3-cyano-4-(benzyloxy)phenyl]-4-methyl-selenazole-5-carboxylic acid (11).

$^1$H NMR (DMSO-$d_6$, 400 MHz) δ 8.34 (d, J=2.4 Hz, 1H), 8.24 (dd, J=2.4, 8.8 Hz, 1H), 7.52-7.38 (m, 6H), 5.38 (s, 2H), 2.65 (s, 3H). MS (EI, m/z): 397.2 [M−H]$^-$.

Embodiment 7

Synthesis of 2-[3-cyano-4-(cyclopropylmethoxy)phenyl]-4-methyl-selenazole-5-carboxylic acid (12)

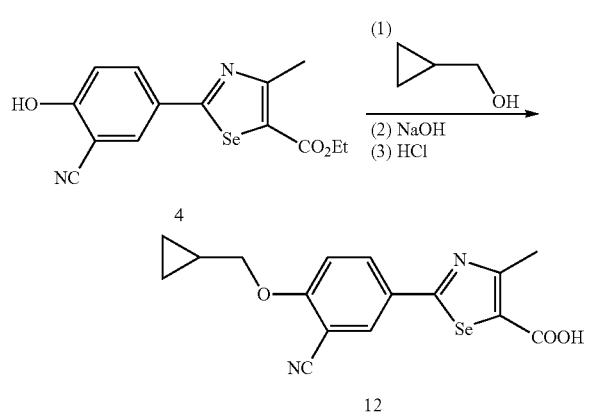

The compound 4 (100 mg, 0.298 mmol) was dissolved in THF (5 mL), added with cyclopropyl methanol (35 mg, 0.485 mmol) and triphenylphosphine (130 mg, 0.496 mmol), and then added dropwise with diethyl diazodicarboxylate (85 mg, 0.488 mmol). The resulting mixture was stirred overnight at room temperature. The solvent was removed by means of reduced pressure distillation, and the resulting product was purified by using a silica column (200 to 300 mesh silica gel, ethyl acetate/petroleum ether=1/20 for elution). The product was then hydrolyzed according to step F in Embodiment 1, and acidized to obtain 2-[3-cyano-4-(cyclopropylmethoxy)phenyl]-4-methyl-selenazole-5-carboxylic acid (12).

$^1$H NMR (DMSO-$d_6$, 400 MHz) δ 8.30 (t, J=1.2 Hz, 1H), 8.22-8.19 (m, 1H), 7.33 (d, J=8.8 Hz, 1H), 4.09 (d, J=7.2 Hz, 2H), 2.65 (s, 3H), 1.30-1.28 (m, 1H), 0.65-0.61 (m, 2H), 0.42-0.40 (m, 2H). MS (EI, m/z): 361.2 [M−H]$^-$.

Embodiment 8

Synthesis of 2-(2-cyano-biphenyl-4-yl)-4-methyl-selenazole-5-carboxylic acid (14)

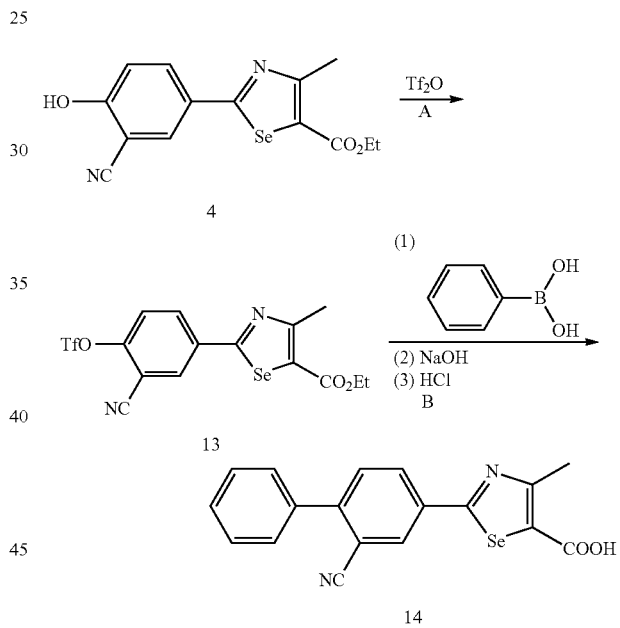

Step A: The compound 4 (7.0 mg, 20.9 mmol) was suspended in anhydrous dichloromethane (100 mL), and then added with DMAP (262 mg, 2.14 mmol) and pyridine (7.0 mL). The resulting mixture was stirred until becoming clear, then cooled by means of an ice-salt bath, and added with trifluoromethanesulfonic anhydride (10.8 mL), and then stirred for 1 h in the ice-salt bath. A TLC analysis indicated that the reaction was completed. The solution was distilled under reduced pressure to remove dichloromethane, then added with a proper amount of water and extracted with ethyl acetate (70 mL×3). The combined organic phase was respectively washed with diluted hydrochloric acid (50 mL) and saturated saline solution (50 mL), and dried with anhydrous sodium sulfate. The solvent was removed by means of reduced pressure distillation, so as to obtain 2-(3-cyano-4-trifluoromethanesulfonyl-phenyl)-4-methyl-selenazole-5-ethyl formate (13) (9.7 g), with a yield of 99%.

Step B(1): A mixture of the compound 13 (110 mg, 0.235 mmol), phenylboronic acid (52.7 mg, 0.422 mmol) and anhydrous potassium carbonate (20 mg, 0.017 mmol) was added with methylbenzene (10 mL) and tetrakis(triphenylphosphine)platinum (20 mg, 0.017 mmol). The resulting mixture was heated to 110° C. under the protection of nitrogen, and stirred overnight. The reaction solution was cooled to room temperature, and filtered with a diatomite pad. The filtrate was purified by using a silica column (200 to 300 mesh silica, ethyl acetate/petroleum ether=1/15 for elution), to obtain 2-(2-cyano-biphenyl-4-yl)-4-methyl-selenazole-5-ethyl formate.

$^1$H NMR (CDCl$_3$, 400 MHz) δ 8.50 (d, J=1.6 Hz, 1H), 8.33 (dd, J=1.6, 8.0 Hz, 1H), 7.64-7.61 (m, 3H), 7.57-7.51 (m, 3H), 4.37 (q, J=6.4 Hz, 2H), 2.82 (s, 3H), 1.42 (t, J=6.4 Hz, 3H).

Step B(2): The ester obtained in step B(1) was hydrolyzed according to step F in Embodiment 1, and acidized to obtain 2-(2-cyano-biphenyl-4-yl)-4-methyl-selenazole-5-carboxylic acid (14).

$^1$H NMR (DMSO-d$_6$, 400 MHz) δ 8.50 (d, J=1.6 Hz, 1H), 8.33 (dd, J=1.6, 8.4 Hz, 1H), 7.77-7.54 (m, 6H), 2.70 (s, 3H). MS (EI, m/z): 367.1 [M−H]$^-$.

Embodiment 9

Synthesis of 2-(2-cyano-3',4'-dimethoxybiphenyl-4-yl)-4-methyl-selenazole-5-carboxylic acid (15)

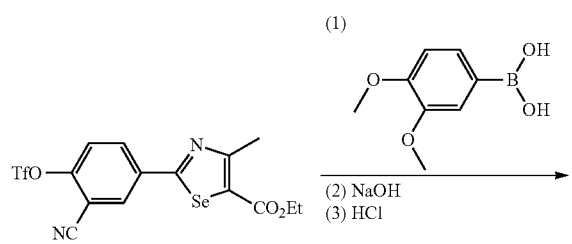

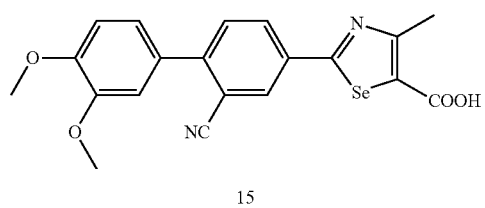

The compound 13 was reacted with 3,4-dimethoxyphenylboronic acid according to step B(1) in Embodiment 8, and was then hydrolyzed according to step F in Embodiment 1, and acidized to obtain 2-(2-cyano-3',4'-dimethoxybiphenyl-4-yl)-4-methyl-selenazole-5-carboxylic acid (15).

$^1$H NMR (DMSO-d$_6$, 400 MHz) δ 8.46 (d, J=2.0 Hz, 1H), 8.30 (dd, J=2.0, 8.4 Hz, 1H), 7.77 (d, J=8.4 Hz, 1H), 7.27-7.22 (m, 2H), 7.14 (d, J=8.4 Hz, 1H), 3.85 (s, 6H), 2.70 (s, 3H). MS (EI, m/z): 427.2 [M−H]$^-$.

Embodiment 10

Synthesis of 2-(2-cyano-3'-fluoro-4'-methoxybiphenyl-4-yl)-4-methyl-selenazole-5-carboxylic acid (16)

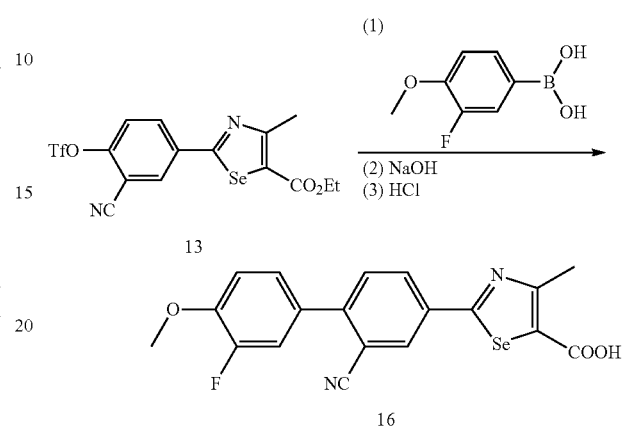

The compound 13 was reacted with 3-fluoro-4-methoxyphenylboronic acid according to step B(1) in Embodiment 8, then hydrolyzed according to step F in Embodiment 1, and acidized to obtain 2-(2-cyano-3'-fluoro-4'-methoxybiphenyl-4-yl)-4-methyl-selenazole-5-carboxylic acid (16).

$^1$H NMR (DMSO-d$_6$, 400 MHz) δ 8.47 (d, J=2.0 Hz, 1H), 8.31 (dd, J=2.0, 8.4 Hz, 1H), 7.75 (d, J=8.4 Hz, 1H), 7.60 (dd, J=2.4, 12.0 Hz, 1H), 7.49-7.47 (m, 1H), 7.37 (t, J=8.8 Hz, 1H), 3.94 (s, 3H), 2.69 (s, 3H). MS (EI, m/z): 415.2 [M−H]$^-$.

Embodiment 11

Synthesis of 2-(2-cyano-3',4',5'-trimethoxybiphenyl-4-yl)-4-methyl-selenazole-5-carboxylic acid (17)

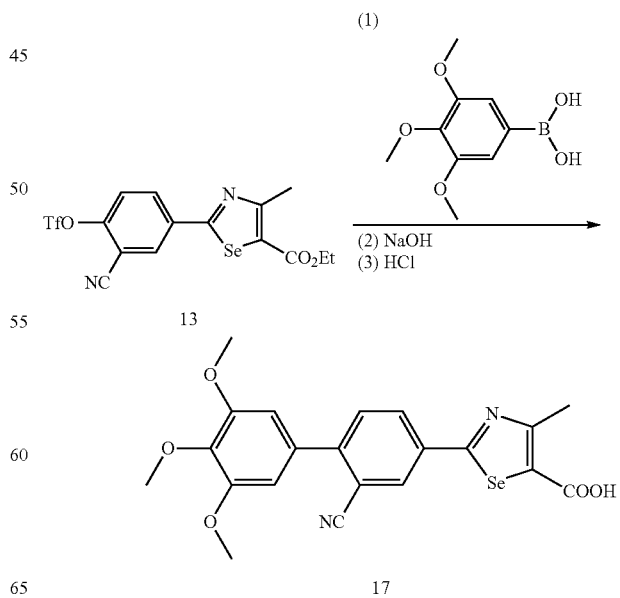

The compound 13 was reacted with 3,4,5-trimethoxyphenylboronic acid according to step B(1) in Embodiment 8, then hydrolyzed according to step F in Embodiment 1, and acidized to obtain 2-(2-cyano-3',4',5'-trimethoxybiphenyl-4-yl)-4-methyl-selenazole-5-carboxylic acid (17).

$^1$H NMR (DMSO-$d_6$, 400 MHz) δ 8.46 (d, J=1.6 Hz, 1H), 8.29 (dd, J=1.6, 8.4 Hz, 1H), 7.81 (d, J=8.4 Hz, 1H), 6.97 (s, 2H), 3.86 (s, 6H), 3.76 (s, 3H), 2.69 (s, 3H). MS (EI, m/z): 457.2 [M−H]$^-$.

Embodiment 12

Synthesis of 2-(2-cyano-4'-methoxybiphenyl-4-yl)-4-methyl-selenazole-5-carboxylic acid (18)

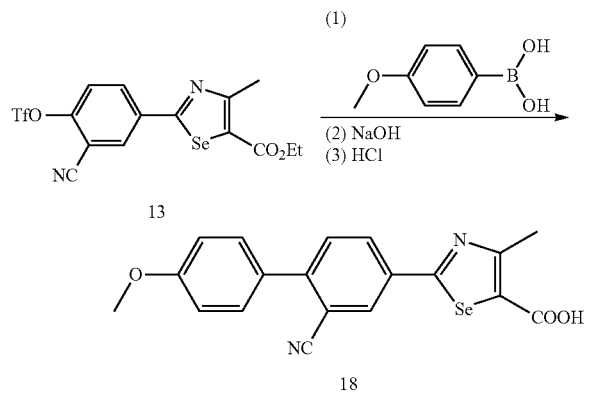

The compound 13 was reacted with 4-methoxyphenylboronic acid according to step B(1) in Embodiment 8, then hydrolyzed according to step F in Embodiment 1, and acidized to obtain 2-(2-cyano-4'-methoxybiphenyl-4-yl)-4-methyl-selenazole-5-carboxylic acid (18).

$^1$H NMR (DMSO-$d_6$, 400 MHz) δ 8.45 (d, J=2.0 Hz, 1H), 8.28 (dd, J=2.0, 8.0 Hz, 1H), 7.71 (d, J=8.4 Hz, 1H), 7.62 (dd, J=2.0, 6.8 Hz, 2H), 7.13 (dd, J=2.0, 6.8 Hz, 2H), 3.85 (s, 3H), 2.69 (s, 3H). MS (EI, m/z): 397.2 [M−H]$^-$.

Embodiment 13

Synthesis of 2-(2-cyano-3'-methoxybiphenyl-4-yl)-4-methyl-selenazole-5-carboxylic acid (19)

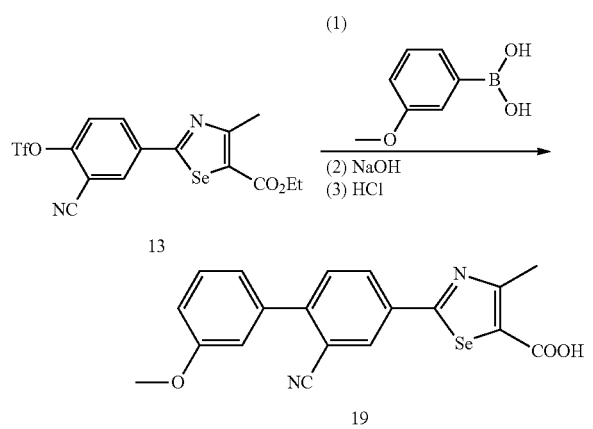

The compound 13 was reacted with 3-methoxyphenylboronic acid according to step B(1) in Embodiment 8, then hydrolyzed according to step F in Embodiment 1, and acidized to obtain 2-(2-cyano-3'-methoxybiphenyl-4-yl)-4-methyl-selenazole-5-carboxylic acid (19).

$^1$H NMR (DMSO-$d_6$, 400 MHz) δ 8.50 (d, J=2.0 Hz, 1H), 8.32 (dd, J=2.0, 8.0 Hz, 1H), 7.77 (d, J=8.4 Hz, 1H), 7.48 (t, J=8.0, 1H), 7.22-7.12 (m, 2H), 7.10-7.09 (m, 1H), 3.85 (s, 3H), 2.70 (s, 1H). MS (EI, m/z): 397.2 [M−H]$^-$.

Embodiment 14

Synthesis of 2-(2-cyano-3'-trifluoromethoxybiphenyl-4-yl)-4-methyl-selenazole-5-carboxylic acid (20)

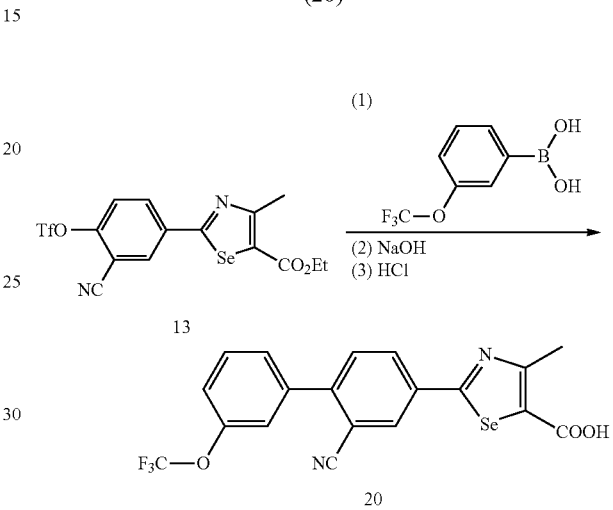

The compound 13 was reacted with 3-trifluoromethoxyphenylboronic acid according to step B(1) in Embodiment 8, then hydrolyzed according to step F in Embodiment 1, and acidized to obtain 2-(2-cyano-3'-trifluoromethoxybiphenyl-4-yl)-4-methyl-selenazole-5-carboxylic acid (20).

$^1$H NMR (DMSO-$d_6$, 400 MHz) δ 8.52 (s, 1H), 8.34 (dd, J=2.0, 8.0 Hz, 1H), 7.81-7.69 (m, 4H), 7.55 (d, J=2.4 Hz, 1H), 2.69 (s, 3H). MS (EI, m/z): 451.2 [M−H]$^-$.

Embodiment 15

Synthesis of 2-(2-cyano-4'-chlorobiphenyl-4-yl)-4-methyl-selenazole-5-carboxylic acid (21)

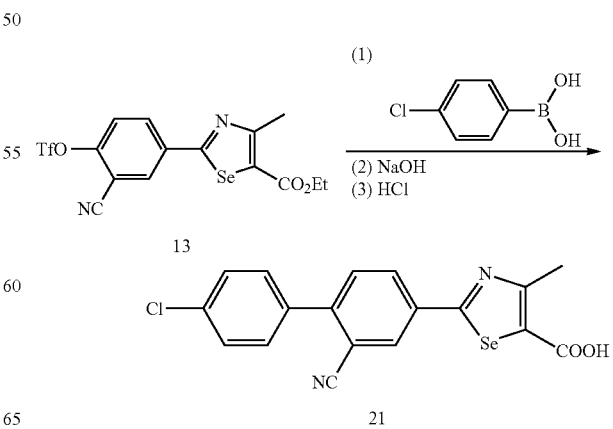

The compound 13 was reacted with 4-chlorophenylboronic acid according to step B(1) in Embodiment 8, then hydrolyzed according to step F in Embodiment 1, and acidized to obtain 2-(2-cyano-4'-chlorobiphenyl-4-yl)-4-methyl-selenazole-5-carboxylic acid (21).

$^1$H NMR (DMSO-d$_6$, 400 MHz) δ 8.51 (d, J=2.0 Hz, 1H), 8.33 (dd, J=2.0, 8.0 Hz, 1H), 7.76 (d, J=8.0, 1H), 7.71-7.64 (m, 4H), 2.69 (s, 3H). MS (EI, m/z): 401.1 [M−H]$^−$.

Embodiment 16

Synthesis of 2-(2-cyano-3',4'-difluorobiphenyl-4-yl)-4-methyl-selenazole-5-carboxylic acid (22)

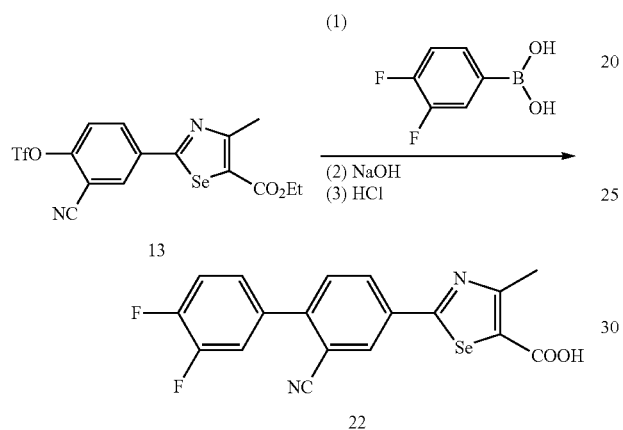

The compound 13 was reacted with 3,4-difluorophenylboronic acid according to step B(1) in Embodiment 8, then hydrolyzed according to step F in Embodiment 1, and acidized to obtain 2-(2-cyano-3',4'-difluorobiphenyl-4-yl)-4-methyl-selenazole-5-carboxylic acid (22).

$^1$H NMR (DMSO-d$_6$, 400 MHz) δ 8.45 (s, 1H), 8.28 (dd, J=2.0, 8.0 Hz, 1H), 7.84-7.74 (m, 2H), 7.69-7.62 (m, 1H), 7.55-7.51 (m, 1H), 2.68 (s, 3H). MS (EI, m/z): 403.1 [M−H]$^−$.

Embodiment 17

Synthesis of 2-(2-cyano-2',3',4',5',6'-pentadeuterobiphenyl-4-yl)-4-methyl-selenazole-5-carboxylic acid (23)

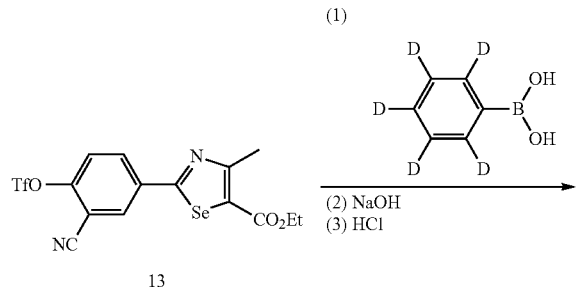

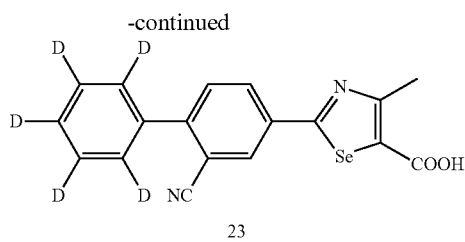

The compound 13 was reacted with 2,3,4,5,6-pentadeuterophenylboronic acid according to step B(1) in Embodiment 8, then hydrolyzed according to step F in Embodiment 1, and acidized to obtain 2-(2-cyano-2',3',4',5',6'-pentadeuterobiphenyl-4-yl)-4-methyl-selenazole-5-carboxylic acid (23).

$^1$H NMR (DMSO-d$_6$, 400 MHz) δ 8.50 (d, J=1.6 Hz, 1H), 8.33 (dd, J=1.6, 8.4 Hz, 1H), 7.76 (d, J=8.4 Hz, 1H), 2.69 (s, 3H). MS (EI, m/z): 372.2 [M−H]$^−$.

Embodiment 18

Synthesis of 2-(2-cyano-2'-methoxybiphenyl-4-yl)-4-methyl-selenazole-5-carboxylic acid (24)

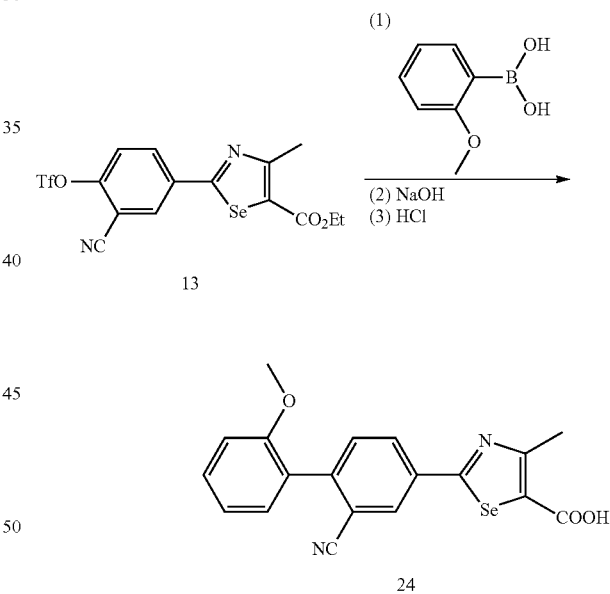

The compound 13 was reacted with 2-methoxyphenylboronic acid according to step B(1) in Embodiment 8, where potassium carbonate was replaced with cesium carbonate. The product was then hydrolyzed according to step F in Embodiment 1, and acidized to obtain 2-(2-cyano-2'-methoxybiphenyl-4-yl)-4-methyl-selenazole-5-carboxylic acid (24).

$^1$H NMR (DMSO-d$_6$, 400 MHz) δ 8.44 (d, J=2.0 Hz, 1H), 8.30 (dd, J=2.0, 8.4 Hz, 1H), 7.63 (d, J=8.0 Hz, 1H), 7.53-7.48 (m, 1H), 7.34 (dd, J=2.0, 7.2 Hz, 1H), 7.21 (d, J=8.0 Hz, 1H), 7.13-7.09 (m, 1H), 3.80 (s, 3H), 2.69 (s, 3H). MS (EI, m/z): 397.1 [M−H]$^−$.

Embodiment 19

Synthesis of 2-(2-cyano-2',4'-dimethoxybiphenyl-4-yl)-4-methyl-selenazole-5-carboxylic acid (25)

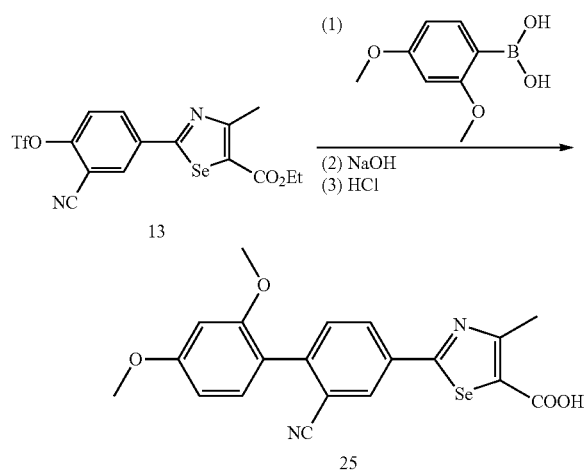

The compound 13 was reacted with 2,4-dimethoxyphenylboronic acid according to step B(1) in Embodiment 8, where potassium carbonate was replaced with cesium carbonate. The product was then hydrolyzed according to step F in Embodiment 1, and acidized to obtain 2-(2-cyano-2',4'-dimethoxybiphenyl-4-yl)-4-methyl-selenazole-5-carboxylic acid (25).

$^1$H NMR (DMSO-$d_6$, 400 MHz) δ 8.40 (d, J=1.6 Hz, 1H), 8.26 (dd, J=1.6, 8.0 Hz, 1H), 7.59 (d, J=8.4 Hz, 1H), 7.27 (d, J=8.4 Hz, 1H), 6.75-6.68 (m, 2H), 3.85 (s, 3H), 3.80 (s, 3H), 2.69 (s, 3H). MS (EI, m/z): 427.2 [M–H]$^-$.

Embodiment 20

Synthesis of 2-[3-cyano-4-(1-naphthyl)-phenyl]-4-methyl-selenazole-5-carboxylic acid (26)

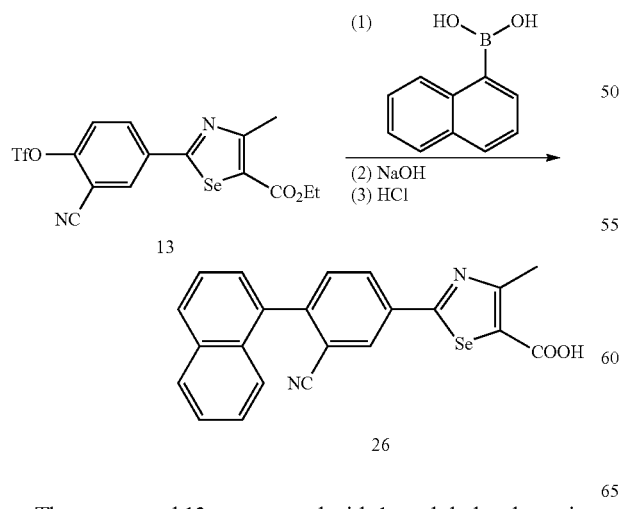

The compound 13 was reacted with 1-naphthaleneboronic acid according to step B(1) in Embodiment 8, then hydrolyzed according to step F in Embodiment 1, and acidized to obtain 2-[3-cyano-4-(1-naphthyl)-phenyl]-4-methyl-selenazole-5-carboxylic acid (26).

$^1$H NMR (DMSO-$d_6$, 400 MHz) δ 8.60 (d, J=2.0 Hz, 1H), 8.40 (dd, J=2.0, 8.0 Hz, 1H), 8.13-8.07 (m, 2H), 7.76-7.54 (m, 6H), 2.72 (s, 3H). MS (EI, m/z): 417.3 [M–H]$^-$.

Embodiment 21

Synthesis of 2-[3-cyano-4-(4-pyridyl)-phenyl-4-yl]-4-methyl-selenazole-5-carboxylic acid (27)

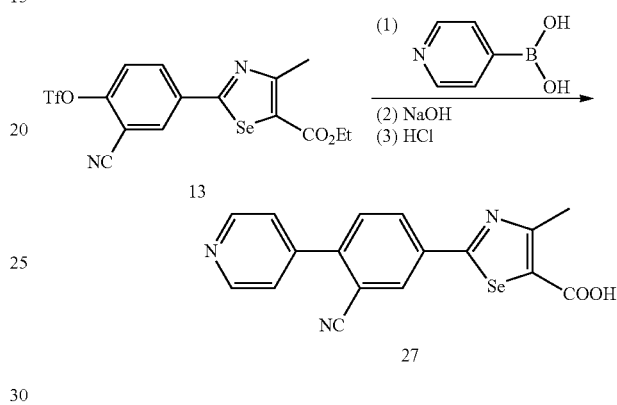

A mixture of the compound 13 (110 mg, 0.235 mmol), 4-pyridineboronic acid (86.8 mg, 0.706 mmol), lithium bromide (102 mg, 1.17 mmol) and sodium carbonate (40 mg, 0.377 mmol) was added with 1,4-dioxane (8 mL) and water (2 mL), and then added with tetrakis(triphenylphosphine)platinum (20 mg, 0.017 mmol). The reaction solution was heated under the protection of nitrogen until reflux occurred, and stirred overnight. After being cooled to room temperature, the solution was filtered with a diatomite pad, and the filtrate was purified by using a silica column (200 to 300 mesh silica gel, ethyl acetate/petroleum ether=1/15 for elution). The resulting product was then hydrolyzed according to step F in Embodiment 1, and acidized to obtain 2-[3-cyano-4-(4-pyridyl)-phenyl-4-yl]-4-methyl-selenazole-5-carboxylic acid (27).

$^1$H NMR (DMSO-$d_6$, 400 MHz) δ 8.81 (s, 2H), 8.58 (d, J=2.0 Hz, 1H), 8.40 (dd, J=2.0, 8.0 Hz, 1H), 7.84 (d, J=8.0 Hz, 1H), 7.71 (d, J=5.6 Hz, 2H), 2.70 (s, 3H). MS (EI, m/z): 368.1 [M–H]$^-$.

Embodiment 22

Synthesis of 2-[3-cyano-4-(3-pyridyl)-phenyl-4-yl]-4-methyl-selenazole-5-carboxylic acid (28)

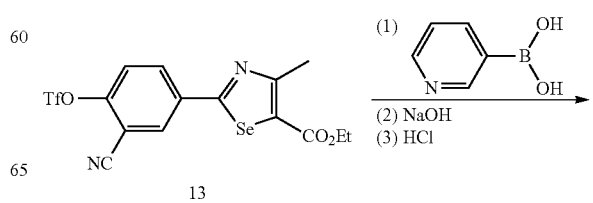

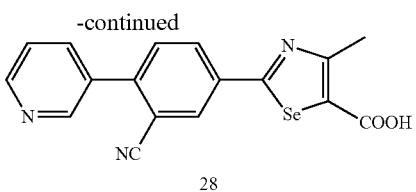

The compound 13 was reacted with 1-naphthaleneboronic acid according to the operation procedure in Embodiment 21, then hydrolyzed according to step F in Embodiment 1, and acidized to obtain 2-[3-cyano-4-(3-pyridyl)-phenyl-4-yl]-4-methyl-selenazole-5-carboxylic acid (28).

$^1$H NMR (DMSO-d$_6$, 400 MHz) δ 8.74 (s, 1H), 8.73 (d, J=5.2 Hz, 1H), 8.55 (d, J=1.6 Hz, 1H), 8.36 (dd, J=2.0, 8.0 Hz, 1H), 8.14-8.11 (m, 1H), 7.83 (d, J=8.0 Hz, 1H), 7.61 (dd, J=4.8, 8.0 Hz, 1H), 2.70 (s, 3H). MS (EI, m/z): 368.1 [M−H]$^-$.

Embodiment 23

Synthesis of 2-[2-cyano-4'-(1.2'-deuteroethyl)-biphenyl-4-yl]-4-methyl-selenazole-5-carboxylic acid (30)

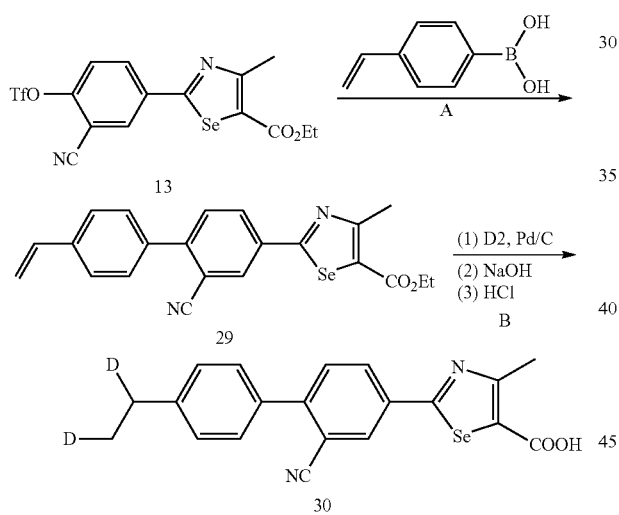

Step A: A mixture of the compound 13 (110 mg, 0.235 mmol), 4-vinylphenylboronic acid (39 mg, 0.264 mmol) and anhydrous potassium carbonate (53 mg, 0.384 mmol) was added with methylbenzene (10 mL) and tetrakis(triphenylphosphine)platinum (20 mg, 0.017 mmol). The reaction solution was heated to 110° C. under the protection of nitrogen, and stirred overnight. The solution was cooled to room temperature, and filtered with a diatomite pad. The filtrate was purified by using a silica column (200 to 300 mesh silica gel, ethyl acetate/petroleum ether=1/20 for elution), to obtain 2-(2-cyano-4'-vinyl-biphenyl-4-yl)-4-methyl-selenazole-5-ethyl formate (29).

Step B: the compound 29 was dissolved in THF (10 mL) and heavy water (1 mL), and added with 5% palladium carbon (20 mg). The mixture was deuterated in deuterium gas under normal pressure for 24 h. After being filtered with diatomite, the filtrate was distilled under reduced pressure so as to remove the solvent. The product was then hydrolyzed according to step F in Embodiment 1, and acidized to obtain 2-[2-cyano-4'-(1.2'-deuteroethyl)-biphenyl-4-yl]-4-methyl-selenazole-5-carboxylic acid (30).

$^1$H NMR (DMSO-d$_6$, 400 MHz) δ 8.48 (d, J=2.0 Hz, 1H), 8.31 (dd, J=2.0, 8.4 Hz, 1H), 7.75 (d, J=8.4 Hz, 1H), 7.58 (d, J=8.4 Hz, 2H), 7.41 (d, J=8.4 Hz, 2H), 2.70-2.68 (m, 4H), 1.23 (t, J=4.0 Hz, 2H). MS (EI, m/z): 397.2 [M−H]$^-$.

Embodiment 24

Synthesis of 2-(2-cyano-6-deuterobiphenyl-4-yl)-4-methyl-selenazole-5-carboxylic acid (35)

Step A: A mixture of the compound 4 (250 mg, 0.745 mmol), methanol (8 mL) and triethylamine (1 mL) was added with NBS (160 mg, 0.898 mmol) in batches in an ice-water bath, and then the resulting mixture was stirred for reaction over 1 h. The solvent was removed by reduced pressure distillation, and the resulting product was dissolved in ethyl acetate (25 mL), filtered to remove insoluble substances, washed with water until the pH value was adjusted to 2-3, and then filtered. The collected solid was directly used for the next step reaction.

Step B: The product obtained in the last step reaction was dissolved in DMF (3 mL), and added with anhydrous potassium carbonate (240 mg, 1.739 mmol) and benzyl bromide (159 mg, 0.930 mmol). The resulting mixture was heated to 60° C. for reaction over about 20 min, and then added with DMF (5 mL) for reaction at constant temperature over 2 h. After being cooled to room temperature, the solution was diluted with water (45 mL), and filtered. The filter cake was dried and then directly used for the next step reaction.

Step C: The product obtained from the last step reaction was dissolved in DMF (10 mL) and heavy water (1 mL), and added with 5% palladium carbon (30 mg). The resulting mixture was deuterated in deuterium gas under normal pressure for 24 h, and filtered with a diatomite pad. The filtrate was distilled under reduced pressure to remove the solvent, so as to obtain 2-(3-cyano-4-hydroxyl-5-deuterophenyl)-4-methyl-selenazole-5-ethyl formate (33) (102 mg), with a total yield of 40.6% in the three steps of reactions.

Step D: The compound 33 (102 mg, 0.302 mmol) was dissolved in dichloromethane (10 mL), added with DMAP (4 mg, 0.033 mmol) and pyridine (0.1 mL), and then added with trifluoromethanesulfonic anhydride (257 mg, 0.910 mmol) in an ice-water bath. The reaction solution was stirred for 1 h in the ice-water bath. Most of dichloromethane was removed by means of reduced pressure distillation. The solution was then added with water (10 mL) and extracted with ethyl acetate (10 mL×3). The combined organic phase was washed with 2M diluted hydrochloric acid (10 mL), and dried with anhydrous sodium sulfate. After the solvent was removed by means of reduced pressure distillation, the product was purified by using a silica column (200 to 300 mesh silica gel, ethyl acetate/petroleum ether=1/20 for elution), to obtain 2-(3-cyano-4-trifluoromethanesulfonyl-5-deuterophenyl)-4-methyl-selenazole-5-ethyl formate (34) (70 mg), with a yield of 49.5%.

Step E: A mixture of the compound 34 (70 mg, 0.149 mmol), phenylboronic acid (33.5 mg, 0.275 mmol) and anhydrous potassium carbonate (33.7 mg, 0.244 mmol) was added with methylbenzene (10 mL) and tetrakis(triphenylphosphine)platinum (20 mg, 0.017 mmol). The reaction solution was heated to 110° C. under the protection of nitrogen, and stirred overnight. After being cooled to room temperature, the reaction solution was filtered with a diatomite pad, and the filtrate was purified by using a silica column (200 to 300 mesh silica gel, ethyl acetate/petroleum ether=1/20 for elution). The resulting product was then hydrolyzed according to step F in Embodiment 1, and acidized to obtain 2-[2-cyano-6-deuterobiphenyl-4-yl]-4-methyl-selenazole-5-carboxylic acid (35).

$^1$H NMR (DMSO-d$_6$, 400 MHz) δ 8.50 (s, 1H), 8.33 (s, 1H), 7.69-7.56 (m, 5H), 2.69 (s, 3H). MS (EI, m/z): 368.2 [M–H]$^-$.

Embodiment 25

Synthesis of 2-(3-cyano-4-isopropylthiophenyl)-4-methyl-selenazole-5-carboxylic acid (37)

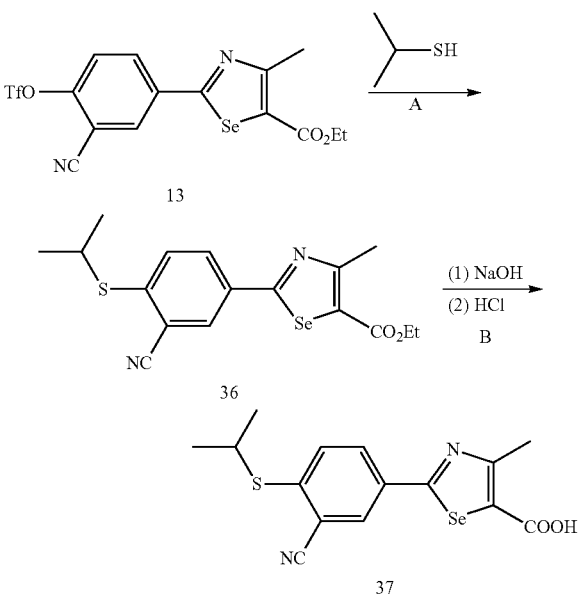

Step A: Under the protection of nitrogen, a three-mouth flask A was successively added with 1,4-dioxane (4 mL), isopropyl mercaptan (27 mg, 0.355 mmol), and diisopropylethylamine (61 mg, 0.472 mmol). The mixed solution was stirred for 40 min at room temperature. Another three-mouth flask B was added with 1,4-dioxane (6 mL), the compound 13 (110 mg, 0.235 mmol), Pd$_2$(dba)$_3$ (11 mg, 0.012 mmol) and 4,5-diphenylphosphine-9,9-dimethylxanthene (13.7 mg, 0.0236 mmol). The mixed solution in the three-mouth flask B was stirred for 20 min under the protection of nitrogen, and then transferred to the aforementioned three-mouth flask A by using a syringe. The resulting mixture was stirred under reflux overnight. After being cooled to room temperature, the reaction solution was added with ethyl acetate (40 mL), washed with water (10 mL×2), and dried with anhydrous sodium sulfate. The solution was purified by using a silica column (200 to 300 mesh silica gel, ethyl acetate/petroleum ether=1/20 for elution), to obtain 2-(3-cyano-4-isopropylthiophenyl)-4-methyl-selenazole-5-ethyl formate (36).

$^1$H NMR (CDCl$_3$, 400 MHz) δ 8.17 (d, J=2.0 Hz, 1H), 8.03 (dd, J=2.0, 8.4 Hz, 1H), 7.51 (d, J=8.4 Hz, 1H), 4.36 (q, J=7.2 Hz, 2H), 3.71-3.63 (m, 1H), 2.79 (s, 3H), 1.43-1.39 (m, 9H).

Step B: The compound 36 was hydrolyzed according to step F in Embodiment 1, and acidized to obtain 2-(3-cyano-4-isopropylthiophenyl)-4-methyl-selenazole-5-carboxylic acid (37).

$^1$H NMR (DMSO-d$_6$, 400 MHz) δ 8.36 (d, J=1.6 Hz, 1H), 8.19 (dd, J=1.6, 8.4 Hz, 1H), 7.71 (d, J=8.4 Hz, 1H), 3.88-3.81 (m, 1H), 2.67 (s, 3H), 1.35 (d, J=6.4 Hz, 6H). MS (EI, m/z): 365.1 [M–H]$^-$.

Embodiment 26

Synthesis of 2-(3-cyano-4-isobutylthiophenyl)-4-methyl-selenazole-5-carboxylic acid (38)

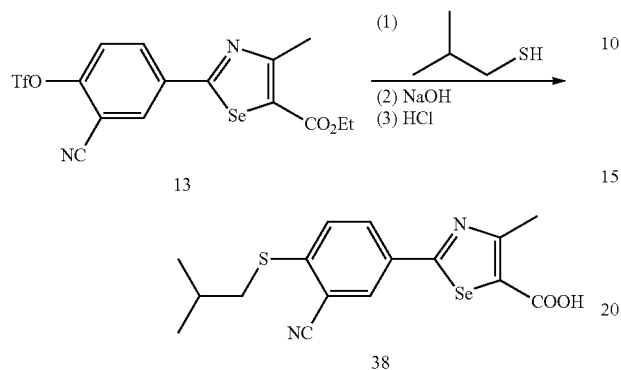

The compound 13 was reacted with isobutyl mercaptan according to step A in Embodiment 25, then hydrolyzed according to step F in Embodiment 1, and acidized to obtain 2-(3-cyano-4-isobutylthiophenyl)-4-methyl-selenazole-5-carboxylic acid (38).

$^1$H NMR (DMSO-d$_6$, 400 MHz) δ 8.33 (d, J=2.0 Hz, 1H), 8.16 (dd, J=2.0, 8.4 Hz, 1H), 7.64 (d, J=8.4 Hz, 1H), 3.09 (d, J=6.4 Hz, 2H), 2.67 (s, 3H), 1.94-1.86 (m, 1H), 1.04 (d, J=6.8 Hz, 6H). MS (EI, m/z): 379.2 [M−H]$^-$.

Embodiment 27

Synthesis of 2-[3-cyano-4-(4-chrolophenylthio)-phenyl]-4-methyl-selenazole-5-carboxylic acid (39)

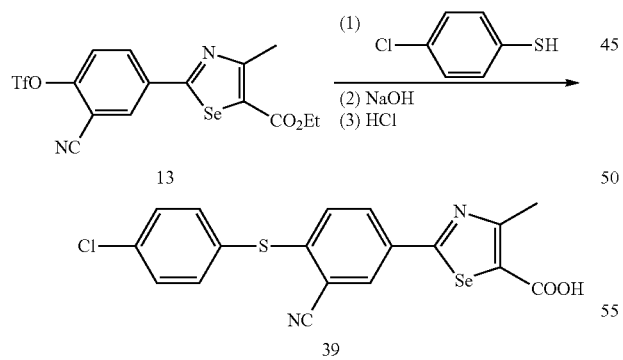

The compound 13 was reacted with 4-chlorothiophenol according to step A in Embodiment 25, then hydrolyzed according to step F in Embodiment 1, and acidized to obtain 2-[3-cyano-4-(4-chrolophenylthio)-phenyl]-4-methyl-selenazole-5-carboxylic acid (39).

$^1$H NMR (DMSO-d$_6$, 400 MHz) δ 8.44 (d, J=2.0 Hz, 1H), 8.15 (dd, J=2.0, 8.4 Hz, 1H), 7.85-7.84 (m, 4H), 7.24 (d, J=8.4 Hz, 1H), 2.65 (s, 3H). MS (EI, m/z): 433.1 [M−H]$^-$.

Embodiment 28

Synthesis of 2-[3-cyano-4-(3-trifluoromethylphenyl-thio)-phenyl]-4-methyl-selenazole-5-carboxylic acid (40)

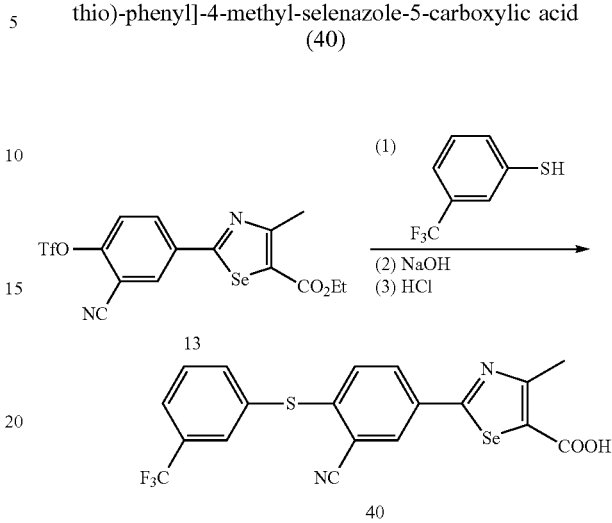

The compound 13 was reacted with 3-trifluoromethylthiophenol according to step A in Embodiment 25, then hydrolyzed according to step F in Embodiment 1, and acidized to obtain 2-[3-cyano-4-(3-trifluoromethylphenyl-thio)-phenyl]-4-methyl-selenazole-5-carboxylic acid (40).

$^1$H NMR (DMSO-d$_6$, 400 MHz) δ 8.49 (d, J=2.0 Hz, 1H), 8.20 (dd, J=2.0, 8.4 Hz, 1H), 7.91 (s, 1H), 7.86-7.71 (m, 3H), 7.36 (d, J=8.4 Hz, 1H), 2.66 (s, 3H). MS (EI, m/z): 467.1 [M−H]$^-$.

Embodiment 29

Synthesis of 2-[3-cyano-4-(2-pyridylthio)-phenyl]-4-methyl-selenazole-5-carboxylic acid (41)

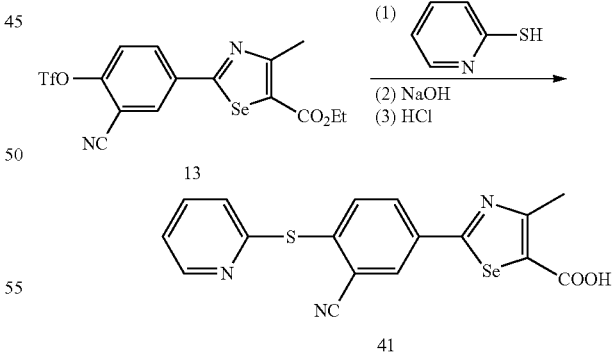

The compound 13 was reacted with 2-mercaptopyridine according to step A in Embodiment 25, then hydrolyzed according to step F in Embodiment 1, and acidized to obtain 2-[3-cyano-4-(2-pyridylthio)-phenyl]-4-methyl-selenazole-5-carboxylic acid (41). $^1$H NMR (DMSO-d$_6$, 400 MHz) δ 8.54 (s, 1H), 8.45-8.43 (m, 1H), 8.29 (dd, J=2.0, 8.0 Hz, 1H), 7.85-7.77 (m, 2H), 7.39 (d, J=8.0 Hz, 1H), 7.31-7.27 (m, 1H), 2.69 (s, 3H). MS (EI, m/z): 400.3 [M−H]$^-$.

Embodiment 30

Synthesis of 2-(3-cyano-4-benzylthio-phenyl)-4-methyl-selenazole-5-carboxylic acid (42)

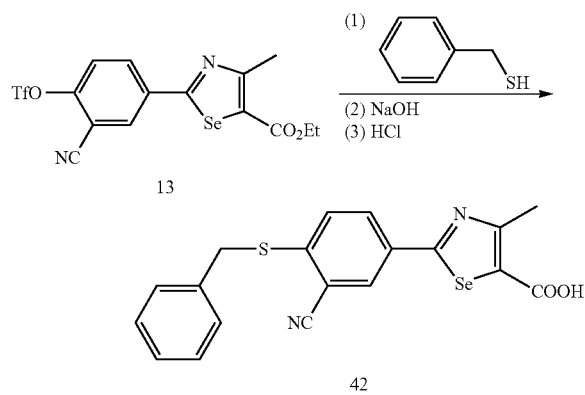

The compound 13 was reacted with 2-mercaptomethyl benzene according to step A in Embodiment 25, then hydrolyzed according to step F in Embodiment 1, and acidized to obtain 2-(3-cyano-4-benzylthio-phenyl)-4-methyl-selenazole-5-carboxylic acid (42). $^1$H NMR (DMSO-$d_6$, 400 MHz) δ 8.35 (d, J=2.0 Hz, 1H), 8.16 (dd, J=2.0, 8.4 Hz, 1H), 7.73 (d, J=8.4 Hz, 1H), 7.47-7.29 (m, 5H), 4.51 (s, 2H), 2.65 (s, 3H). MS (EI, m/z): 413.3 [M−H]$^-$.

Embodiment 31

Synthesis of 2-(3-cyano-4-isopropyl sulfone-phenyl)-4-methyl-selenazole-5-carboxylic acid (43)

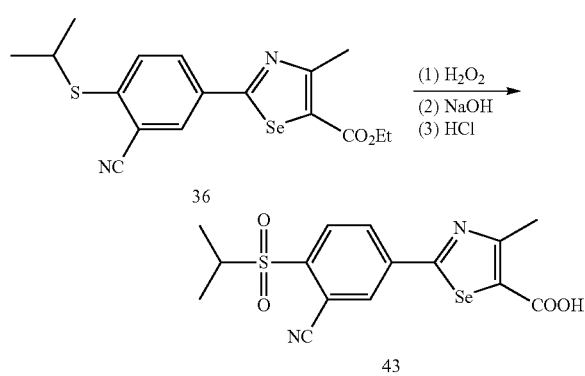

The compound 36 (80 mg, 0.203 mmol) was dissolved in acetic acid (5 mL), and the resulting solution was added with hydrogen peroxide (1.5 mL), and then stirred overnight at room temperature. The reaction solution was added with water (20 mL) for dilution and filtered. The filter cake was then collected. The obtained product was hydrolyzed according to step F in Embodiment 1, and acidized to obtain 2-(3-cyano-4-isopropyl sulfone-phenyl)-4-methyl-selenazole-5-carboxylic acid (43).

$^1$H NMR (DMSO-$d_6$, 400 MHz) δ 13.56 (s, 1H), 8.71 (d, J=2.0 Hz, 1H), 8.52 (dd, J=2.0, 8.4 Hz, 1H), 8.17 (d, J=8.4 Hz, 1H), 3.65 (t, J=6.8 Hz, 1H), 2.71 (s, 3H), 1.26 (d, J=6.8 Hz, 6H). MS (EI, m/z): 397.1 [M−H]$^-$.

Embodiment 32

Synthesis of 2-(3-cyano-4-morpholinyl-4-yl-phenyl)-4-methyl-selenazole-5-carboxylic acid (44)

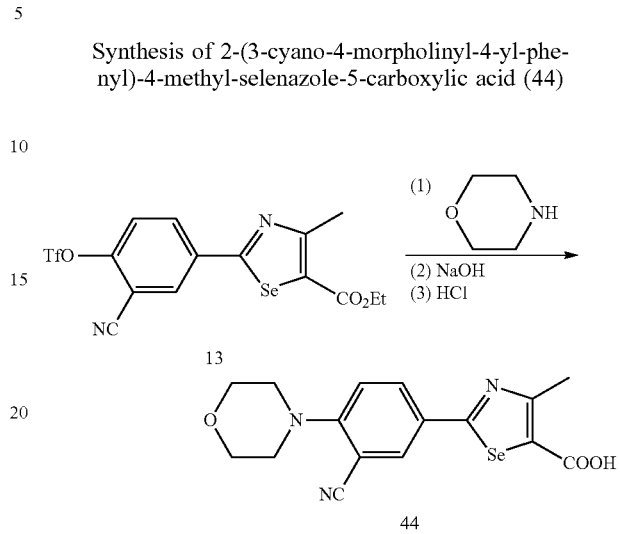

The compound 13 (100 mg, 0.214 mmol) was added into morpholine (3 mL). The resulting reaction solution was heated to 80° C., stirred for 15 min, then cooled to room temperature, and added with water (20 mL) for dilution. After filtration, the filter cake was collected. The obtained product was hydrolyzed according to step F in Embodiment 1, and acidized to obtain 2-(3-cyano-4-morpholinyl-4-yl-phenyl)-4-methyl-selenazole-5-carboxylic acid (44).

$^1$H NMR (DMSO-$d_6$, 400 MHz) δ 8.24 (d, J=2.0 Hz, 1H), 8.13 (dd, J=2.0, 8.8 Hz, 1H), 7.22 (d, J=8.8 Hz, 1H), 3.78 (d, J=4.0 Hz, 4H), 3.31 (d, J=4.0 Hz, 4H), 2.64 (s, 3H). MS (EI, m/z): 367.2 [M−H]$^-$.

Embodiment 33

Synthesis of 2-[3-cyano-4-(4-methylpiperazin-1-yl)phenyl]-4-methyl-selenazole-5-carboxylic acid (45)

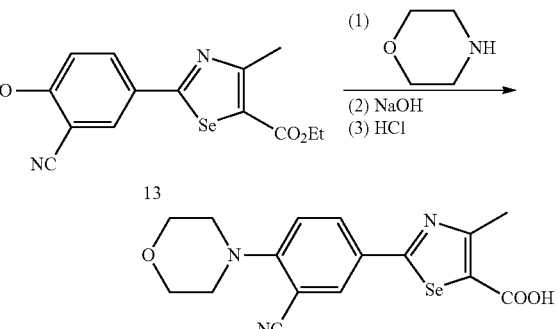

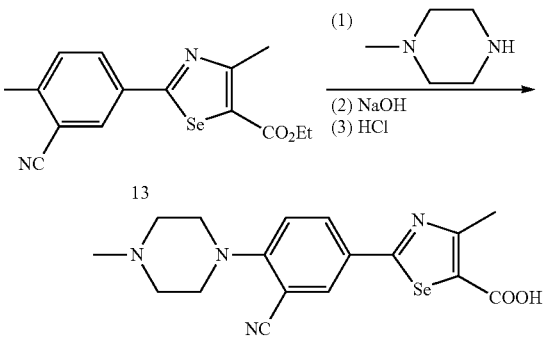

The compound 13 was reacted with methylpiperidine according to the experimental procedure in Embodiment 32, then hydrolyzed according to step F in Embodiment 1, and acidized to obtain 2-[3-cyano-4-(4-methylpiperazin-1-yl)phenyl]-4-methyl-selenazole-5-carboxylic acid (45).

¹H NMR (DMSO-d₆, 400 MHz) δ 8.30 (d, J=2.0 Hz, 1H), 8.16 (dd, J=2.0, 8.8 Hz, 1H), 7.32 (d, J=8.8 Hz, 1H), 3.65-3.14 (m, 8H), 2.81 (s, 3H), 2.64 (s, 3H). MS (EI, m/z): 389.1 [M−H]⁻.

Embodiment 34

Synthesis of 2-{3-cyano-4-(6,7-dihydro-4H-thieno[3,2-c]pyridyl)-phenyl}-4-methyl-selenazole-5-carboxylic acid (46)

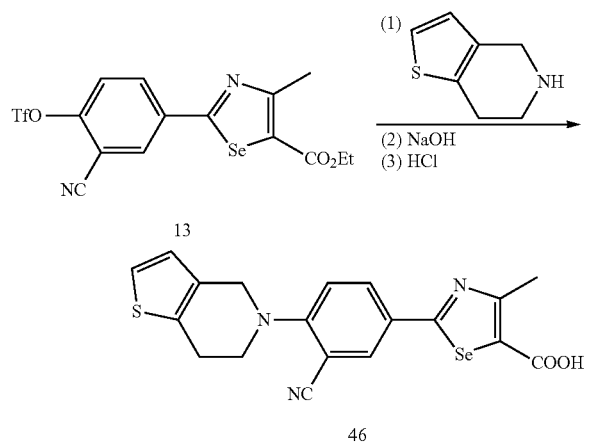 [SMILES: CCOC(=O)c1[se]c(-c2ccc(OS(=O)(=O)C(F)(F)F)c(C#N)c2)nc1C ; c1cc2c(s1)CCNC2 ; Cc1nc(-c2ccc(N3CCc4sccc4C3)c(C#N)c2)[se]c1C(=O)O]

4,5,6,7-4H-thieno[3,2-c]pyridine hydrochloride (173 mg, 0.984 mmol) was dissolved in DMF (5 mL). The resulting solution was added with the compound 13 (100 mg, 0.214 mmol) and diisopropylethylamine (138 mg, 1.067 mmol), then heated to 90° C. and stirred for 40 min. After being cooled to room temperature, the solution was poured into water (30 mL), and then extracted with ethyl acetate (15 mL×3). The organic phase was washed with water (10 mL×2), and the solvent was removed by means of reduced pressure distillation. The product was purified by using a silica column (200 to 300 mesh silica, ethyl acetate/petroleum ether=1/15 for elution). The obtained product was hydrolyzed according to step F in Embodiment 1, and acidized to obtain 2-{3-cyano-4-(6,7-dihydro-4H-thieno[3,2-c]pyridyl)-phenyl}-4-methyl-selenazole-5-carboxylic acid (46).

¹H NMR (DMSO-d₆, 400 MHz) δ 8.25 (d, J=2.4 Hz, 1H), 8.11 (d, J=2.4, 8.8 Hz, 1H), 7.39 (d, J=5.2 Hz, 1H), 7.26 (d, J=5.2 Hz, 1H), 6.93 (d, J=5.2 Hz, 1H), 4.45 (s, 2H), 3.78 (t, J=5.2 Hz, 2H), 3.03 (t, J=5.2 Hz, 2H), 2.64 (s, 3H). MS (EI, m/z): 428.2 [M−H]⁻.

Embodiment 35

Synthesis of 2-(3-cyano-4-dimethylamino-phenyl)-4-methyl-selenazole-5-carboxylic acid (47)

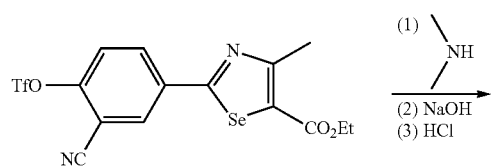

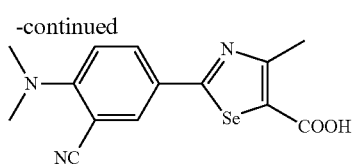

The compound 13 (150 mg, 0.321 mmol) was dissolved in DMF (4.5 mL), and then added with 30% dimethylamine aqueous solution (1.5 mL). The reaction solution was stirred for 2 h at room temperature, then added with water (20 mL) for dilution, and extracted with ethyl acetate (10 mL×3). The organic phase was washed with water (10 mL×2), and distilled under reduced pressure to remove the solvent. The product was purified by using a silica column (200 to 300 mesh silica gel, ethyl acetate/petroleum ether=1/15 for elution). The obtained product was hydrolyzed according to step F in Embodiment 1, and acidized to obtain 2-(3-cyano-4-dimethylamino-phenyl)-4-methyl-selenazole-5-carboxylic acid (47).

¹H NMR (DMSO-d₆, 400 MHz) δ 8.10 (d, J=2.4 Hz, 1H), 7.98 (dd, J=2.4, 9.2 Hz, 1H), 7.03 (d, J=9.2 Hz, 1H), 3.15 (s, 6H), 2.63 (s, 3H). MS (EI, m/z): 334.2 [M−H]⁻.

Embodiment 36

Synthesis of 2-(3-chloro-4-isobutoxyphenyl)-4-methyl-selenazole-5-carboxylic acid (51)

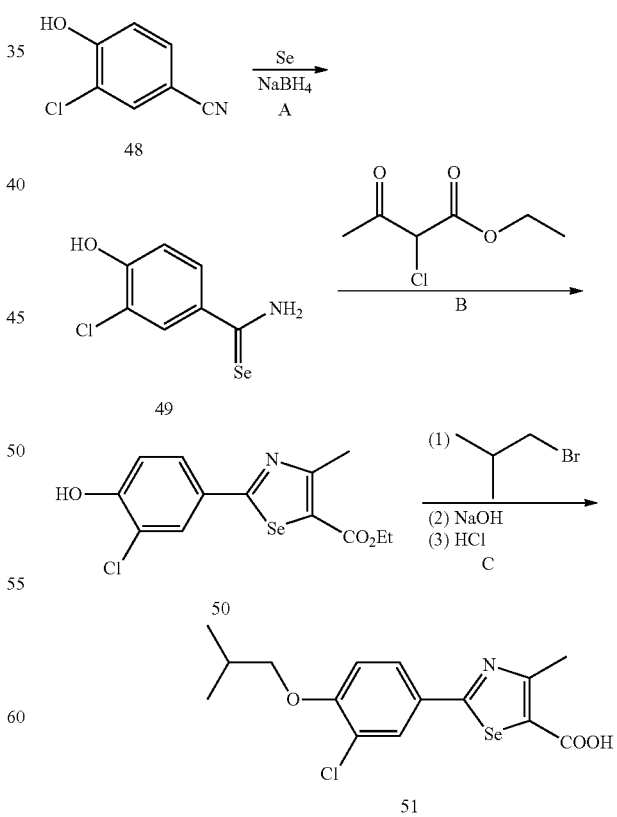

Step A: At 0-10° C., anhydrous ethanol (36 mL) was slowly added into a mixture of selenium powder (3.3 g, 41.8 mmol) and sodium borohydride (1.73 g, 45.8 mmol), then heated to room temperature and stirred for 30 min, and then added with pyridine solution (8.3 mL) containing 3-chloro-4-hydroxybenzonitrile (1.6 g, 10.4 mmol). The reaction solution was heated until reflux occurred, then slowly added dropwise with 2M hydrochloric acid (21 mL), and stirred under reflux for 1 h. A TLC analysis indicated that the reaction was completed. The reaction solution was cooled to room temperature, added with water (100 mL) for dilution and extracted with ethyl acetate (30 mL×3). The combined organic phase was respectively washed with 2M hydrochloric acid (15 mL×2) and saturated saline solution (20 mL). The solvent was removed by means of reduced pressure distillation, so as to obtain 3-chloro-4-hydroxy selenobenzamide (49) (2.4 g), with a yield of 98.1%.

Step B: The compound 49 (2.4 g, 10.2 mmol) was dissolved in ethanol (25 mL), and added with ethyl 2-chloroacetoacetate (2.04 g, 12.4 mmol). The mixed solution was heated until reflux occurred, and stirred for 2 h. A TLC analysis indicated that the reaction was completed. The reaction solution was cooled to room temperature, and was dried after suction filtration to obtain 2-(3-chloro-4-hydroxyphenyl)-4-methyl-selenazole-5-ethyl formate (50) (3.1 g), with a yield of 88.1%.

Step C: The compound 50 (80 mg, 0.232 mmol) was dissolved in DMF (5 mL), and then added with potassium iodide (8.0 mg, 0.048 mmol), anhydrous potassium carbonate (42.6 mg, 0.309 mmol), and 1-bromo-2-methylpropane (49.4 mg, 0.361 mmol). The resulting mixture was heated to 70° C. and stirred overnight. After being cooled to room temperature, the mixture was added with water (20 mL) for dilution and filtered. The filter cake was purified by using a silica column (200 to 300 mesh silica gel, ethyl acetate/petroleum ether=1/15 for elution). The obtained product was hydrolyzed according to step F in Embodiment 1, and acidized to obtain 2-(3-chloro-4-isobutoxyphenyl)-4-methyl-selenazole-5-carboxylic acid (51).

$^1$H NMR (DMSO-d$_6$, 400 MHz) δ 13.24 (s, 1H), 7.99 (s, 1H), 7.88 (d, J=8.8 Hz, 1H), 7.24 (d, J=8.8 Hz, 1H), 3.93 (d, J=6.4 Hz, 2H), 2.64 (s, 3H), 2.12-2.05 (m, 1H), 1.02 (d, J=6.8 Hz, 6H). MS (EI, m/z): 372.1 [M−H]$^-$.

Embodiment 37

Synthesis of 2-(3-trifluoromethyl-4-isobutoxyphenyl)-4-methyl-selenazole-5-carboxylic acid (55)

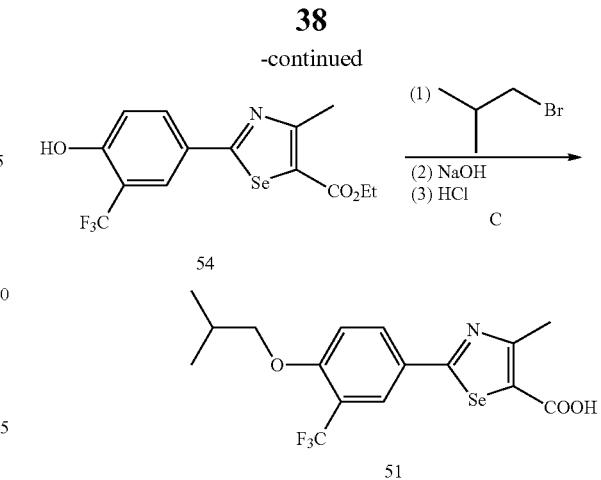

A compound 3-trifluoromethyl-4-hydroxybenzonitrile was used to prepare selenoamide according to step A in Embodiment 32, then cyclized according to step B in Embodiment 32 and reacted with 1-bromo-2-methylpropane according to step C in Embodiment 32, and finally hydrolyzed according to step F in Embodiment 1 and acidized to obtain 2-(3-trifluoromethyl-4-isobutoxyphenyl)-4-methyl-selenazole-5-carboxylic acid (55).

$^1$H NMR (DMSO-d$_6$, 400 MHz) δ 8.18 (dd, J=2.4, 8.8 Hz, 1H), 8.13 (d, J=2.4 Hz, 1H), 7.36 (d, J=9.2 Hz, 1H), 3.99 (d, J=6.0 Hz, 2H), 2.65 (s, 3H), 2.10-2.03 (m, 1H), 1.01 (d, J=6.8 Hz, 6H). MS (EI, m/z): 406.3 [M−H]$^-$.

Embodiment 38

Synthesis of 2-[3-cyano-4-(isopropylthiomethyl)-phenyl]-4-methyl-selenazole-5-carboxylic acid (62)

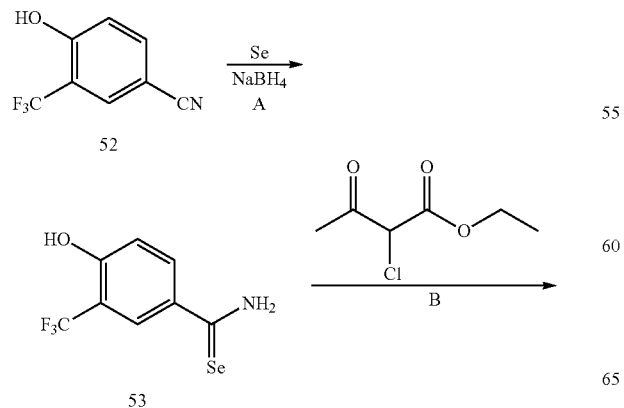
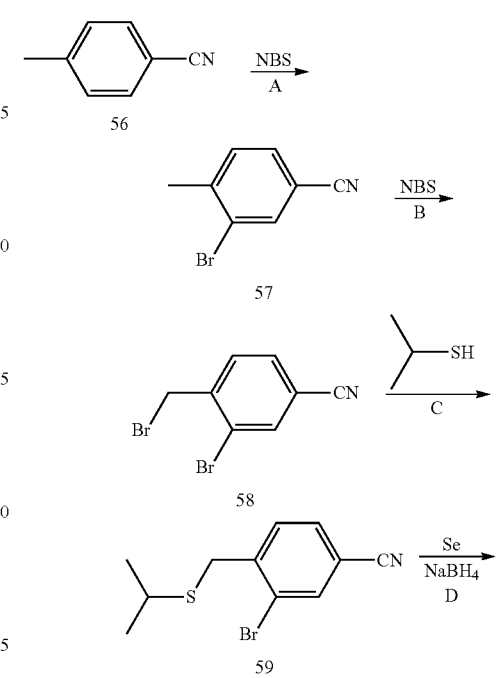

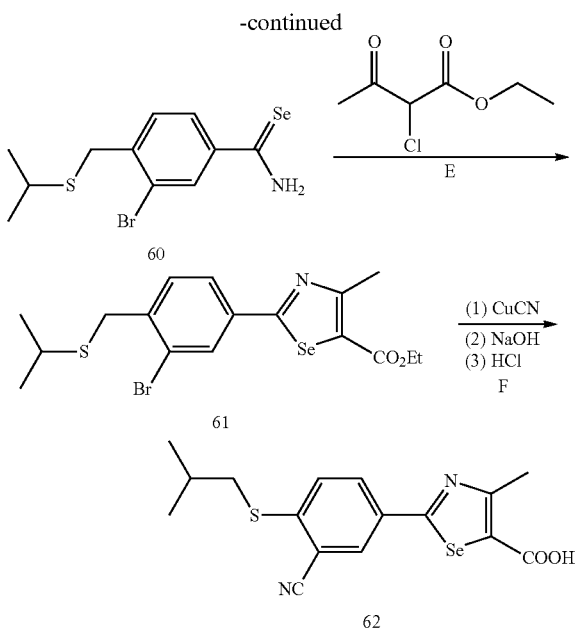

Step A: Concentrated sulfuric acid (20 mL) was added into water (20 mL) to prepare sulfuric acid solution, and the resulting solution was then added with 4-methylbenzonitrile (5.86 g, 50.0 mmol) and NBS (8.9 g, 50.0 mmol). The resulting mixture was stirred overnight at room temperature while being protected from light. After filtration, the filter cake was dissolved in ethyl acetate (150 mL), respectively washed with water (30 mL×2), sodium bicarbonate aqueous solution (30 mL) and saturated saline solution (20 mL), and dried with anhydrous sodium sulfate. The solvent was removed by means of reduced pressure distillation, so as to obtain 3-bromo-4-methylbenzonitrile (57) (6.78 g), with a yield of 69.2%.

$^1$H NMR (CDCl$_3$, 400 MHz) δ 7.84 (d, J=1.6 Hz, 1H), 7.52 (dd, J=1.6, 8.0 Hz, 1H), 7.35 (d, J=8.0 Hz, 1H).

Step B: The compound 57 (804 mg, 4.04 mmol) was dissolved in carbon tetrachloride (8 mL), and then added with NBS (730 mg, 4.10 mmol) and benzoyl peroxide (7 mg, 0.0289 mmol). The resulting mixture was heated under the protection of nitrogen until reflux occurred, and was stirred overnight. The mixture was cooled to room temperature, filtered to remove insoluble substances and distilled under reduced pressure to remove the solvent, then dissolved in ethyl acetate (30 mL) and respectively washed with water (10 mL) and saturated saline solution (10 mL). After the solvent was removed by means of reduced pressure distillation, the resulting product was purified by using a silica column (200 to 300 mesh silica gel, ethyl acetate/petroleum ether=1/35 for elution) to obtain 3-bromo-4-cyanobenzyl bromide (58) (583 mg), with a yield of 52.5%.

Step C: The compound 58 (275 mg, 1.0 mmol) was dissolved in DMF (5 mL), cooled to 0-10° C., and added with cesium carbonate (652 mg, 2.0 mmol) and isopropyl mercaptan (114 mg, 1.5 mmol), heated to room temperature and stirred for 2 h. A TLC analysis indicated that the reaction was completed. The reaction solution was added with water (30 mL), and extracted with ethyl acetate (15 mL×3). The combined organic phase was then washed with water (10 mL×2) and dried with anhydrous sodium sulfate. The solvent was removed by means of reduced pressure distillation, so as to obtain an oily substance, 3-bromo-4-isopropyl cyanobenzyl sulfide (59) (278 mg), with a yield of 100%.

Step D: At 0-10° C., anhydrous ethanol (10 mL) was slowly added into selenium powder (340 mg, 4.306 mmol) and sodium borohydride (178 mg, 4.709 mmol), then heated to room temperature and stirred for 30 min. The resulting mixture was then added with pyridine solution (1.5 mL) containing the compound 59 (270 m, 1.0 mmol), heated until reflux occurred, and slowly added dropwise with 2M hydrochloric acid solution (10 mL). After addition, the solution was stirred under reflux for 1 h. A TLC analysis indicated that the reaction was completed. The solution was cooled to room temperature, added with water (30 mL) for dilution, and extracted with ethyl acetate (15 mL×3). The combined organic phase was respectively washed with 2M hydrochloric acid (15 mL) and saturated saline solution (15 mL). The solvent was removed by means of reduced pressure distillation, so as to obtain a product, 3-bromo-4-isopropylthiomethyl selenobenzamide (60), which was directly used for the next step reaction.

Step E: The compound 60 was dissolved in ethanol (10 mL), added with ethyl 2-chloroacetoacetate (248 mg, 1.506 mmol), then heated until reflux occurred and stirred for 2 h. After ethanol was removed by means of reduced pressure distillation, the resulting product was purified by using a silica column (200 to 300 mesh silica gel, ethyl acetate/petroleum ether=1/20 for elution), to obtain 2-[3-bromo-4-(isopropylthiomethyl)phenyl]-4-methyl-selenazole-5-ethyl formate (61) (118 mg), with a yield of 25.6%.

Step F: The compound 61 (115 mg, 0.249 mmol) was dissolved in N-methylpyrrolidone (6 mL), added with cuprous cyanide (40 mg, 0.446 mmol), then heated under the protection of nitrogen until reflux occurred, and stirred for 6 h. After the solvent was removed by means of reduced pressure distillation, the resulting product was purified by using a silica column (200 to 300 mesh silica gel, ethyl acetate/petroleum ether=1/15 for elution), to obtain 2-[3-cyano-4-(isopropylthiomethyl)phenyl]-4-methyl-selenazole-5-ethyl formate.

$^1$H NMR (CDCl$_3$, 400 MHz) δ 8.16 (d, J=1.6 Hz, 1H), 7.83 (dd, J=1.6, 8.0 Hz, 1H), 7.50 (d, J=8.0 Hz, 1H), 4.36 (q, J=6.8 Hz, 2H), 3.90 (s, 2H), 2.95-2.89 (m, 1H), 2.81 (s, 3H), 1.40 (t, J=2.8 Hz, 3H), 1.30 (d, J=10.0 Hz, 6H).

The ester was hydrolyzed according to step F in Embodiment 1, and acidized to obtain 2-[3-cyano-4-(isopropylthiomethoxy)phenyl]-4-methyl-selenazole-5-carboxylic acid (62).

$^1$H NMR (DMSO-d$_6$, 400 MHz) δ 8.38 (d, J=2.0 Hz, 1H), 8.22 (dd, J=2.0, 8.4 Hz, 1H), 7.70 (d, J=8.4 Hz, 1H), 3.98 (s, 2H), 2.90-2.83 (m, 1H), 2.67 (s, 3H), 1.23 (d, J=6.8 Hz, 6H). MS (EI, m/z): 379.1 [M−H]$^-$.

Embodiment 39

Synthesis of 2-[3-bromo-4-(aniline formyl)-phenyl]-4-methyl-selenazole-5-carboxylic acid (67)

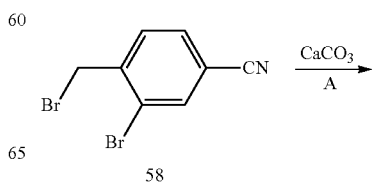

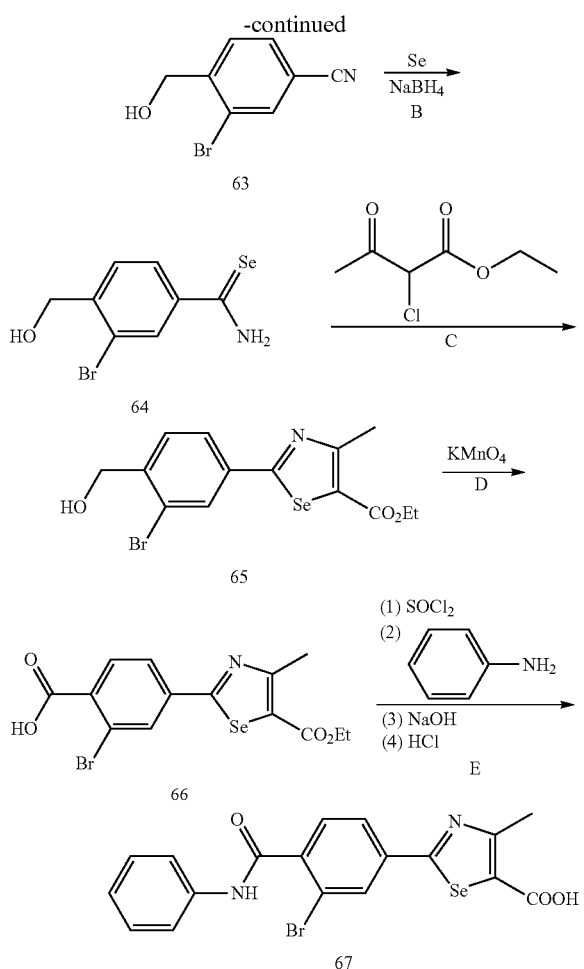

Step A: The compound 58 (2.6 g, 9.46 mmol) was dissolved in 1,4-dioxane (20 mL) and water (20 mL), then added with calcium carbonate (4.3 g, 43 mmol), heated until reflux occurred and stirred overnight. The solution was cooled to room temperature, added with water (40 mL) and extracted with ethyl acetate (30 mL×3). The combined organic phase was filtered with a short silicone pad. The solvent was removed by means of reduced pressure distillation, so as to obtain 3-bromo-4-hydroxymethyl benzonitrile (63) (1.8 g), with a yield of 89.7%.

Step B: At 0-10° C., anhydrous ethanol (27 mL) was slowly added dropwise into a mixture of selenium powder (2.7 g, 34.2 mmol) and sodium borohydride (1.57 g, 41.5 mmol), then heated to room temperature and stirred for 30 min, and then added with pyridine solution (7.2 mL) containing 3-bromo-4-isopropylthiomethyl benzonitrile (63) (1.8 g, 8.49 mmol). The reaction solution was heated until reflux occurred, slowly added dropwise with 2M hydrochloric acid solution (18 mL) and then stirred under reflux for 1 h. A TLC analysis indicated that the reaction was completed. The solution was cooled to room temperature, added with a proper amount of water and then extracted with ethyl acetate (30 mL×3). The organic phase was respectively washed with 2M hydrochloric acid (20 mL) and saturated saline solution (20 mL), and dried with anhydrous sodium sulfate. The solvent was removed by means of reduced pressure distillation, so as to obtain pink 3-bromo-4-hydroxymethyl selenobenzamide (64) (1.98 g), with a yield of 79.6%.

Step C: The compound 64 (293 mg, 1.0 mmol) was dissolved in ethanol (10 mL), added with ethyl 2-chloroacetoacetate (197 mg, 1.20 mmol), and then heated under reflux for 1.5 h. A TLC analysis indicated that the reaction was completed. The solution was cooled to room temperature, added with a proper amount of water, and filtered to obtain a compound 2-(3-bromo-4-hydroxymethylphenyl)-4-methyl-selenazole-5-ethyl formate (65) (340 mg), with a yield of 84.3%.

Step D: The compound 65 (200 mg, 0.496 mmol) was dissolved in acetone (5 mL), and then added with potassium permanganate (158 mg, 1.0 mmol). After being stirred at room temperature for 2 h, the resulting mixture was quenched with sodium hydrogen sulfite aqueous solution, added with a proper amount of water, and filtered to remove insoluble substances. The filtrate was extracted with ethyl acetate (20 mL×2), and the water phase was added with 2M hydrochloric acid to adjust the pH value to 3-4. After filtration, 2-(3-bromo-4-carboxylphenyl)-4-methyl-selenazole-5-ethyl formate (66) (168 mg) was obtained, with a yield of 81.2%.

Step E: The compound 66 (147 mg, 0.352 mmol) was dissolved in dichloromethane (10 mL), and then added with thionyl chloride (168 mg, 1.41 mmol). The resulting solution was heated until reflux occurred, then stirred for 3 h, and distilled under reduced pressure to remove the solvent. The product was then added with dichloromethane (10 mL), and added with triethylamine (107 mg, 1.059 mmol) and aniline (33 mg, 0.354 mmol) while being cooled in an ice-water bath. After the ice-water bath was removed, the solution was stirred at room temperature for 1 h. The reaction solution was washed with a proper amount of water and dried with anhydrous sodium sulfate. The solvent was removed by means of reduced pressure distillation, and the product was purified by using a silica column (200 to 300 mesh silica gel, ethyl acetate/petroleum ether=1/15 for elution). The obtained product was hydrolyzed according to step F in Embodiment 1, and acidized to obtain 2-[3-bromo-4-(aniline formyl)-phenyl]-4-methyl-selenazole-5-carboxylic acid (67).

¹H NMR (DMSO-d₆, 400 MHz) δ 10.62 (s, 1H), 8.26 (d, J=1.6 Hz, 1H), 8.07 (dd, J=1.6, 8.0 Hz, 1H), 7.73-7.67 (m, 3H), 7.37 (t, J=8.0 Hz, 2H), 7.14 (d, J=8.0 Hz, 1H), 2.69 (s, 3H). MS (EI, m/z): 435.1 [M+H]⁺.

Embodiment 40

Synthesis of 2-(2-cyano-4'-trifluoromethylbiphenyl-4-yl)-4-methyl-selenazole-5-carboxylic acid (68)

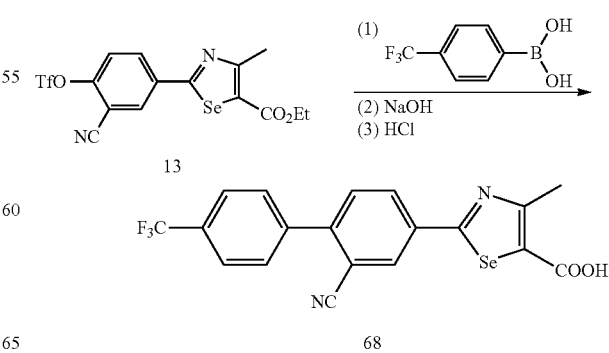

The compound 13 was reacted with 4-trifluoromethoxyphenylboronic acid according to step B(1) in Embodiment 8, then hydrolyzed according to step F in Embodiment 1, and acidized to obtain 2-(2-cyano-4'-trifluoromethylbiphenyl-4-yl)-4-methyl-selenazole-5-carboxylic acid (68).

$^1$H NMR (DMSO-d$_6$, 400 MHz) δ 8.55 (d, J=2.0 Hz, 1H), 8.38 (dd, J=2.0, 8.0 Hz, 1H), 7.95 (d, J=8.0 Hz, 2H), 7.89 (d, J=8.4 Hz, 2H), 7.82 (d, J=8.4 Hz, 1H), 2.66 (s, 3H). MS (EI, m/z): 434.8 [M−H]$^-$.

Embodiment 41

Synthesis of 2-(2-cyano-3'-trifluoromethylbiphenyl-4-yl)-4-methyl-selenazole-5-carboxylic acid (69)

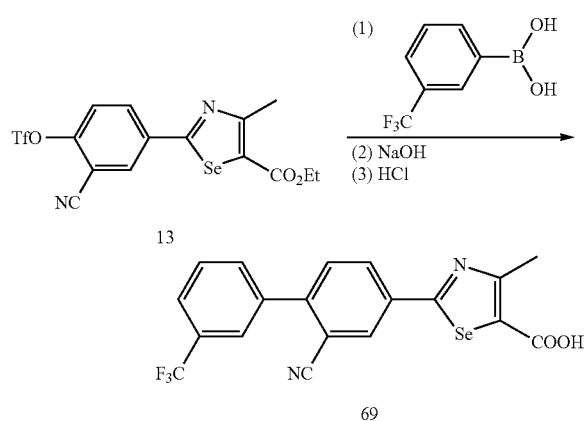

For the experimental operation, refer to step B in Embodiment 8, where potassium carbonate was replaced with cesium carbonate in the reaction (1).

The compound 13 was reacted with 3-trifluoromethoxyphenylboronic acid according to step B(1) in Embodiment 8, where potassium carbonate was replaced with cesium carbonate. The product was then hydrolyzed according to step F in Embodiment 1, and acidized to obtain 2-(2-cyano-3'-trifluoromethylbiphenyl-4-yl)-4-methyl-selenazole-5-carboxylic acid (69).

$^1$H NMR (DMSO-d$_6$, 400 MHz) δ 8.55 (d, J=2.0 Hz, 1H), 8.37 (dd, J=2.0, 8.4 Hz, 1H), 8.03-7.81 (m, 5H), 2.70 (s, 3H). MS (EI, m/z): 434.8 [M−H]$^-$.

Embodiment 42

Synthesis of 2-(2-cyano-3'-trifluoromethylbiphenyl-4-yl)-4-methyl-selenazole-5-carboxylic acid (70)

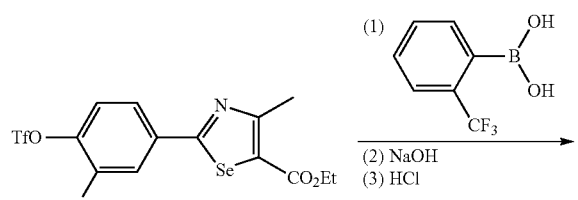

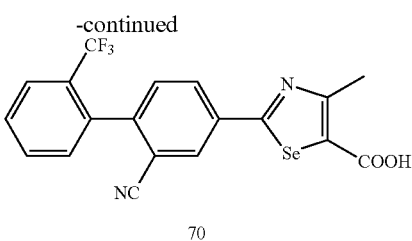

The compound 13 was reacted with 2-trifluoromethoxyphenylboronic acid according to step B(1) in Embodiment 8, then hydrolyzed according to step F in Embodiment 1, and acidized to obtain 2-(2-cyano-3'-trifluoromethylbiphenyl-4-yl)-4-methyl-selenazole-5-carboxylic acid (70).

$^1$H NMR (DMSO-d$_6$, 400 MHz) δ 8.34 (dd, J=1.6, 8.0 Hz, 1H), 8.32 (d, J=2.0 Hz, 1H), 7.95 (d, J=8.0 Hz, 1H), 7.86-7.56 (m, 4H), 2.70 (s, 3H). MS (EI, m/z): 434.8 [M−H]$^-$.

Embodiment 43

Synthesis of 2-(3-cyano-4-isobutoxyphenyl)-4-hydroxymethyl-selenazole-5-carboxylic acid (74)

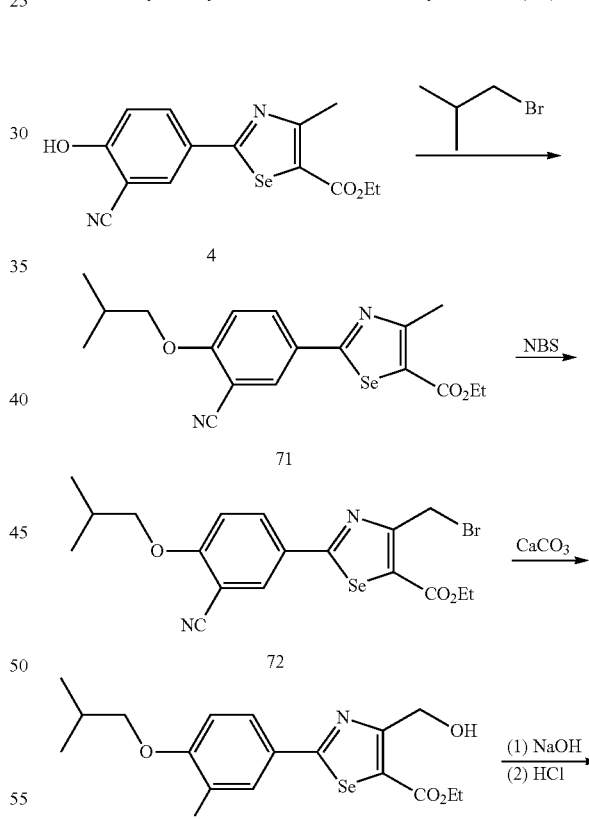

Step A: The compound 4 (1.0 g, 2.983 mmol) was dissolved in DMF (10 mL), and added with anhydrous potassium carbonate (1.2 g, 8.70 mmol) and 1-bromo-2-methylpropane (0.82 g, 5.985 mmol), and the resulting mixture was stirred overnight at 80° C. The mixture was cooled to room temperature, added with water for dilution, and then filtered. The filter cake was purified by using a silica column (200 to 300 mesh silica gel, ethyl acetate/petroleum ether=1/20 for elution), to obtain 2-(3-cyano-4-isobutoxyphenyl)-4-methyl-selenazole-5-ethyl formate (71) (1.10 g), with a yield of 94.2%.

Step B: The compound 71 (1.1 g, 2.811 mmol) was dissolved in carbon tetrachloride (25 mL), and then added with NBS (0.55 g, 3.090 mmol) and benzoyl peroxide (0.40 g, 1.65 mmol). The resulting mixture was heated under the protection of nitrogen until reflux occurred, and then stirred overnight. After the solvent was removed by means of reduced pressure distillation, the product was purified by using a silica column (200 to 300 mesh silica gel, ethyl acetate/petroleum ether=1/5 for elution), to obtain 2-(3-cyano-4-isobutoxyphenyl)-4-bromomethyl-selenazole-5-ethyl formate (72) (0.91 g), with a yield of 68.8%.

Step C: The compound 72 (0.90 g, 1.914 mmol) was dissolved in 1,4-dioxane (15 mL) and water (15 mL), then added with calcium carbonate (0.80 g, 8.0 mmol), heated until reflux occurred and stirred overnight under reflux. The solution was cooled to room temperature, added with water (30 mL) and extracted with ethyl acetate (30 mL×3). The organic solvent was removed by means of reduced pressure distillation, and the product was purified by using a silica column (200 to 300 mesh silica gel, ethyl acetate/petroleum ether=1/5 for elution), so as to obtain 2-(3-cyano-4-isobutoxyphenyl)-4-hydroxymethyl-selenazole-5-ethyl formate (73) (0.20 g), with a yield of 25.7%.

Step D: The compound 73 was hydrolyzed according to step F in Embodiment 1, and acidized to obtain 2-(3-chloro-4-isobutoxyphenyl)-4-hydroxymethyl-selenazole-5-carboxylic acid (74).

$^1$H NMR (DMSO-d$_6$, 400 MHz) δ 8.36 (d, J=2.0 Hz, 1H), 8.25 (dd, J=2.0, 8.8 Hz, 1H), 7.37 (d, J=8.8 Hz, 1H), 4.81 (s, 2H), 4.02 (d, J=6.4 Hz, 2H), 2.15-2.05 (m, 1H), 1.02 (d, J=6.4 Hz, 6H). MS (EI, m/z): 379.0 [M–H]$^-$.

Embodiment 44

Synthesis of 2-(3-bromo-4-isobutoxyphenyl)-4-methyl-selenazole-5-carboxylic acid (78)

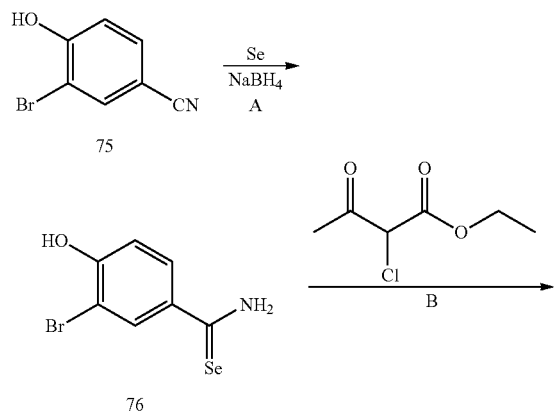

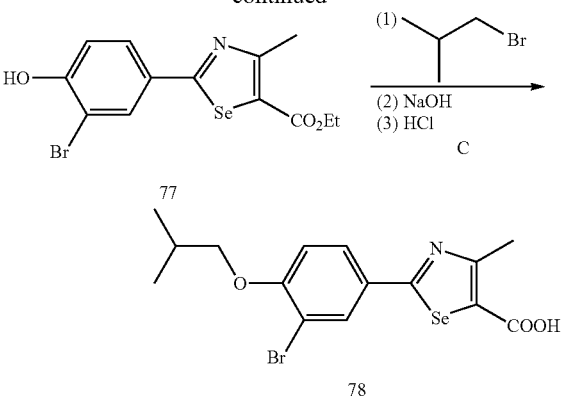

A compound 3-bromo-4-hydroxybenzonitrile was used to prepare selenoamide according to step A in Embodiment 36, then cyclized according to step B in Embodiment 32 and reacted with 1-bromo-2-methylpropane according to step C in Embodiment 32, and finally hydrolyzed according to step F in Embodiment 1 and acidized to obtain 2-(3-bromo-4-isobutoxyphenyl)-4-methyl-selenazole-5-carboxylic acid (78). $^1$H NMR (DMSO-d$_6$, 400 MHz) δ 8.13 (d, J=2.0 Hz, 1H), 7.91 (dd, J=2.4, 8.8 Hz, 1H), 7.19 (d, J=8.8 Hz, 1H), 3.92 (d, J=6.4 Hz, 2H), 2.64 (s, 3H), 2.11-2.03 (m, 1H), 1.02 (q, J=6.8 Hz, 6H). MS (EI, m/z): 416.0 [M–H]$^-$.

Embodiment 45

Synthesis of 2-(3-cyano-4-isopropylthiophenyl)-4-methyl-selenazole-5-carboxylic acid-(2-N-acetyl) ethyl ester (79)

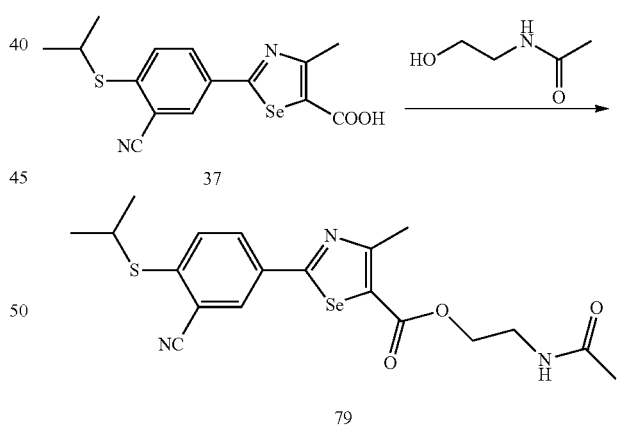

A mixture of the compound 37 (120 mg, 0.328 mmol), N-(2-hydroxyethyl)acetamide (50.8 mg, 0.493 mmol), N-methylmorpholine (99.7 mg, 0.985 mmol), HOBT (66.6 mg, 0.493 mmol) and DMF (5 mL) was added with EDCI in an ice-water bath, and then stirred overnight at room temperature. The reaction solution was added with water (20 mL), and extracted with ethyl acetate (15 mL×3). The combined organic phase was then washed with water (15 mL) once more. After the solvent was removed by means of reduced pressure distillation, the product was purified by using a silica column (200 to 300 mesh silica gel, ethyl acetate for elution), to obtain 2-(3-cyano-4-isopropylthiophenyl)-4-methyl-selenazole-5-carboxylic acid-(2-N-acetyl)ethyl ester (79).

$^1$H NMR (DMSO-$d_6$, 400 MHz) δ 8.39 (d, J=2.0 Hz, 1H), 8.22-8.19 (m, 1H), 8.07-8.04 (m, 1H), 7.72 (dd, J=4.0, 8.4 Hz, 1H), 4.24 (t, J=5.2 Hz, 2H), 3.89-3.82 (m, 1H), 3.41-3.29 (m, 2H), 2.68 (s, 3H), 1.87 (s, 3H), 1.37-1.36 (m, 6H). MS (EI, m/z): 449.9 [M−H]$^-$.

The compound 79 may be a prodrug of the compound 37.

Embodiment 46

Synthesis of 2-(3-cyano-4-tertbutylthiophenyl)-4-methyl-selenazole-5-carboxylic acid (81)

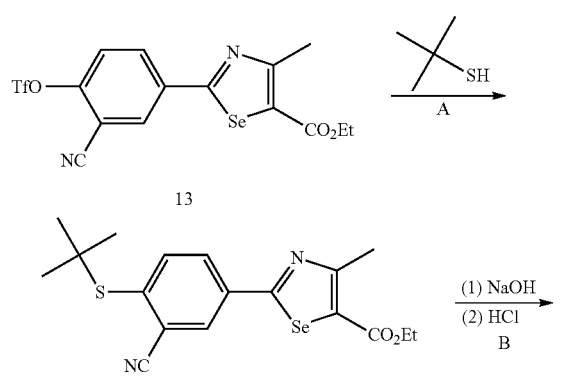

The compound was reacted with tert-butyl mercaptan according to step A in Embodiment 25, then hydrolyzed according to step F in Embodiment 1, and acidized to obtain 2-(3-cyano-4-tertbutylthiophenyl)-4-methyl-selenazole-5-carboxylic acid (81).

$^1$H NMR (DMSO-$d_6$, 400 MHz) δ 8.47 (d, J=2.0 Hz, 1H), 8.26 (dd, J=2.0, 8.4 Hz, 1H), 7.86 (d, J=8.4 Hz, 1H), 2.68 (s, 3H), 1.36 (s, 9H). MS (EI, m/z): 381.4 [M+H]$^+$.

Embodiment 47

Synthesis of 2-(3-cyano-4-cyclohexylthiophenyl)-4-methyl-selenazole-5-carboxylic acid (83)

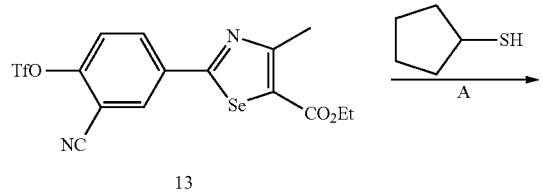

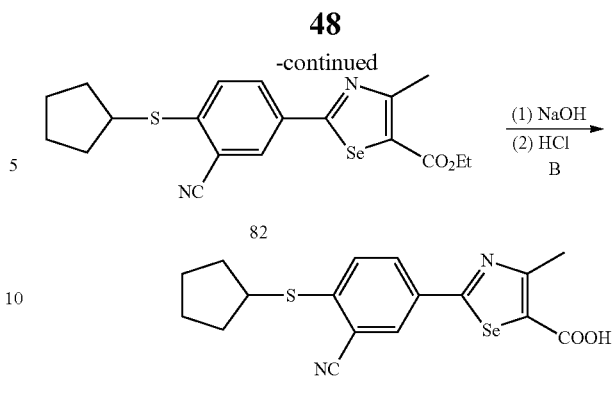

The compound was reacted with cyclopentyl mercaptan according to step A in Embodiment 25, then hydrolyzed according to step F in Embodiment 1, and acidized to obtain 2-(3-cyano-4-cyclohexylthiophenyl)-4-methyl-selenazole-5-carboxylic acid (83).

$^1$H NMR (DMSO-$d_6$, 400 MHz) δ 8.34 (d, J=2.0 Hz, 1H), 8.18 (dd, J=2.0, 8.4 Hz, 1H), 7.69 (d, J=2.0 Hz, 1H), 4.01-3.96 (m, 1H), 2.66 (s, 3H), 2.22-2.17 (m, 2H), 1.76-1.74 (m, 2H), 1.67-1.64 (m, 4H). MS (EI, m/z): 393.1 [M+H]$^+$.

Embodiment 48

Synthesis of 2-(3-trifluoromethylphenyl)-4-methyl-selenazole-5-carboxylic acid (86)

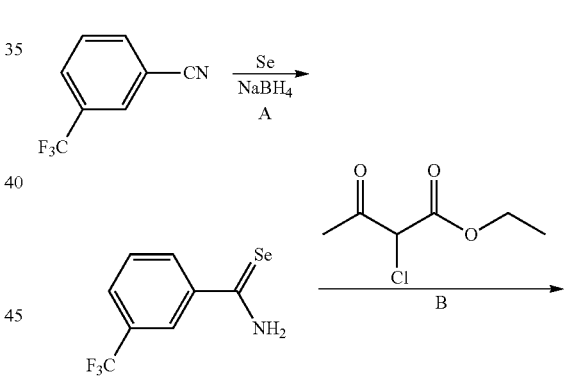

Step A: Anhydrous ethanol (30 mL) was added dropwise into a mixture of selenium powder (1.84 g, 23.3 mmol) and sodium borohydride (0.97 g, 25.6 mmol) under the protection of nitrogen in an ice-water bath, then heated to room temperature, and stirred for 30 min. The resulting mixture was then added with pyridine solution (6 mL) containing 3-(trifluoromethyl)benzonitrile (1.0 g, 5.84 mmol), heated until reflux occurred, and slowly added dropwise with 2M hydrochloric acid solution (4 mL) and then stirred under reflux for 1 h. A TLC analysis indicated that the reaction was completed. Most of ethanol was removed by means of reduced pressure distillation. The resulting product was added with water (30 mL) for dilution, and extracted with ethyl acetate (20 mL×3). The combined organic phase was washed with 2M hydrochloric acid (10 mL) and then with saturated saline solution (15 mL). The solvent was removed by means of reduced pressure distillation, so as to obtain a compound 3-trifluoromethyl selenobenzamide (84) (1.6 g), which was directly used for the next step reaction without being purified.

Step B: the compound 84 (1.0 g, NMT 3.65 mmol) and ethyl 2-chloroacetoacetate (653 mg, 3.97 mmol) were added into anhydrous ethanol (10 mL), heated, and stirred under reflux for 2 h. A TLC analysis indicated that the reaction was completed. The reaction solution was cooled to room temperature. After suction filtration under reduced pressure, the filter cake was collected and dried, to obtain 2-(3-trifluoromethylphenyl)-4-methyl-selenazole-5-ethyl formate (85) (930 mg), with a total yield of 70.3% in the two steps of reactions.

Step C: The compound 85 was hydrolyzed according to step F in Embodiment 1, and acidized to obtain 2-(3-trifluoromethylphenyl)-4-methyl-selenazole-5-carboxylic acid (86).

$^1$H NMR (DMSO-$d_6$, 400 MHz) δ 8.26-8.23 (m, 2H), 7.92 (d, J=8.0 Hz, 1H), 7.77-7.73 (m, 1H), 2.68 (s, 3H).

Embodiment 49

Test for Inhibition of the Activity of Xanthine Oxidase

I. Principle

The inhibition of the activity of xanthine oxidase (XO) is tested through a coupled enzymatic reaction of xanthine oxidase, horseradish peroxidase (HRP) and a substrate thereof. First, xanthine oxidase oxidizes hypoxanthine to produce xanthine and hydrogen peroxide, and further oxidizes xanthine to produce uric acid and hydrogen peroxide. Then, hydrogen peroxide reacts with 10-acetyl-3,7-dihydroxyphenoxazine (Ampliflu Red) under catalytic action of horseradish peroxidase so as to produce resorufin, a compound with strong fluorescence. The fluorescence intensity of resorufin is determined by using a fluorescence microplate, which is in direct proportion to the activity of xanthine oxidase.

II. Test Compound and Preparation of Reaction Solutions

A certain amount of a test compound and a control compound, febuxostat (by Beijing Lianben Pharm-chemicals Tech. Co., Ltd.) were dissolved in DMSO (by Sinopharm Chemical Reagent Co., Ltd.). A 2.5-fold serial dilution of the test compound was diluted with DMSO in a 96-well polypropylene reaction plate (by Greiner Bio One), so as to obtain a 200-fold dilution. The solution was further diluted in ultrapure water to obtain a 3-fold serial dilution.

Reaction solution A: 6 mU/mL xanthine oxidase (sourced from milk, by Sigma) was prepared in 0.1 M Tris-HCl (pH 7.5) buffer solution.

Reaction solution B: A mixed solution of 0.6 U/mL horseradish peroxidase (by Shanghai Yuanye Biological Technology Co., Ltd.), 0.15 mM Ampliflu Red (by Sigma), and 0.3 mM hypoxanthine (by Sigma) was prepared in 0.1 M Tris-HCl (pH 7.5) buffer solution. The solution was placed away from light at 4° C., and used immediately after preparation.

III. Determination Method

9 μL reaction solution A and 9 μL 3-fold serial dilution of the test compound were mixed in a 96-well test plate (by Greiner Bio One), placed on a flat plate type oscillator, and mixed at 30° C. for 30 min at 100 rpm. 9 μL reaction solution B was then added. A enzymatic reaction was carried out for 30 min at 30° C. The fluorescence intensity at 530 nm exciting light and 590 nm emitted light was determined by using a fluorescence microplate (Perkin Elmer Vitor X4). The fluorescence intensity without xanthine oxidase for comparison is 0%, and the fluorescence intensity without the test compound for comparison is 100%, according to which 50% inhibition concentration ($IC_{50}$) of the test compound and control compound febuxostat was calculated.

For the test results, refer to Table 1. It can be shown from Table 1 that, the compound of the present invention exhibited an excellent effect of xanthine oxidase inhibition in a pharmacological test in vitro.

TABLE 1

Xanthine Oxidase Inhibition Activity ($IC_{50}$) of Compounds

| Compound No. | $IC_{50}$ (nM) |
|---|---|
| Compound 6 | 2.29 |
| Compound 7 | 2.05 |
| Compound 8 | 2.40 |
| Compound 9 | 3.28 |
| Compound 10 | 12.43 |
| Compound 11 | 2.85 |
| Compound 12 | 2.97 |
| Compound 14 | 1.70 |
| Compound 15 | 3.25 |
| Compound 16 | 2.99 |
| Compound 17 | 3.79 |
| Compound 18 | 2.70 |
| Compound 19 | 4.61 |
| Compound 20 | 3.92 |
| Compound 21 | 2.61 |
| Compound 22 | 3.24 |
| Compound 23 | 2.37 |
| Compound 24 | 1.67 |
| Compound 25 | 3.47 |
| Compound 26 | 2.78 |
| Compound 27 | 2.53 |
| Compound 28 | 2.67 |
| Compound 30 | 4.84 |
| Compound 35 | 2.63 |
| Compound 37 | 1.32 |
| Compound 38 | 2.56 |
| Compound 39 | 3.58 |
| Compound 40 | 12.06 |
| Compound 41 | 5.19 |
| Compound 42 | 3.07 |
| Compound 43 | 13.89 |
| Compound 44 | 2.30 |
| Compound 45 | 9.13 |
| Compound 46 | 4.11 |
| Compound 47 | 2.52 |
| Compound 51 | 10.25 |
| Compound 55 | 3.06 |
| Compound 62 | 8.56 |
| Compound 67 | >100 |
| Compound 68 | 2.84 |
| Compound 69 | 6.01 |
| Compound 70 | 31.07 |
| Compound 74 | 10.08 |
| Compound 81 | 2.29 |
| Compound 83 | 2.43 |
| Compound 86 | 25.45 |
| Febuxostat | 2.78 |

What is claimed is:

1. A compound represented by formula (I) or a pharmaceutically acceptable salt thereof,

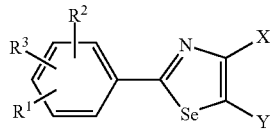

(I)

wherein,
X is selected from C$_{1-2}$ alkyl or substituted C$_{1-2}$ alkyl;
Y is selected from —COOR$^a$ or —CONHR$^a$;
R$^1$ is selected from halogen, —CN, C$_{1-2}$ alkyl, substituted C$_{1-2}$ alkyl, C$_{1-3}$ alkoxy, or substituted C$_{1-3}$ alkoxy;
R$^2$ is selected from H, D, halogen, C$_{1-2}$ alkyl, substituted C$_{1-2}$ alkyl, C$_{1-3}$ alkoxy, or substituted C$_{1-3}$ alkoxy; and
R$^3$ is selected from —(CH$_2$)$_n$—O—R$^b$, —(CH$_2$)$_n$—S—R$^b$, —C(O)R$^b$, —NR$^c$R$^d$, —S(O)CHR$^c$R$^d$, —S(O)$_2$CHR$^c$R$^d$, —(CH$_2$)$_n$C(O)NR$^c$R$^d$, aryl, substituted aryl, a heterocyclic radical, a substituted heterocyclic radical, a heteroaryl radical, or a substituted heteroaryl radical, wherein,
n is 0 to 2;
R$^a$ is selected from H, C$_{1-6}$ alkyl or substituted C$_{1-6}$ alkyl;
R$^b$ is selected from H, methyl, ethyl, propyl, 2-propyl, butyl, tertiary butyl, amyl, substituted C$_{1-8}$ alkyl, aryl, substituted aryl, a heterocyclic radical, a substituted heterocyclic radical, a heteroaryl radical, or a substituted heteroaryl radical; and
R$^c$ and R$^d$ are respectively independently selected from H, C$_{1-8}$ alkyl, or substituted C$_{1-8}$ alkyl; or R$^c$ and R$^d$ are cyclized to form cycloalkyl, substituted cycloalkyl, a heteroaryl radical, or a substituted heteroaryl radical; and
a substituent in groups X, Y, R$^1$, R$^2$, R$^3$, R$^a$, R$^b$, R$^c$ or R$^d$ is selected from one or more of D, —OH, —CN, —NH$_2$, acyl, acylamino, halogen, C$_{1-4}$ alkyl, halogenated C$_{1-4}$ alkyl, deuterated C$_{1-4}$ alkyl, C$_{1-2}$alkoxy, or C$_{1-2}$ alkylamino.

2. The compound according to claim 1, wherein the compound is a compound represented by formula (II), or a pharmaceutically acceptable salt thereof

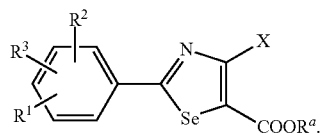

(II)

3. The compound according to claim 2, wherein X is —CH$_3$, —CH$_2$CH$_3$, —CH$_2$OH, or —CF$_3$.

4. The compound according to claim 3, wherein R$^a$ is H, C$_{1-3}$ alkyl, or substituted C$_{1-3}$ alkyl.

5. The compound according to claim 4, wherein R$^1$ is selected from halogen, —CN, —CH$_3$, —CH$_2$CH$_3$, —CF$_3$, —OCHF$_2$, or —OCF$_3$.

6. The compound according to claim 5, wherein R$^2$ is selected from H or D.

7. The compound according to claim 6, wherein the compound is a compound represented by formula (III), or a pharmaceutically acceptable salt thereof

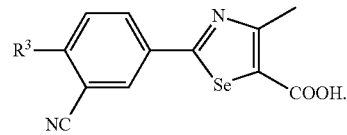

(III)

8. The compound according to claim 7, wherein,
R$^3$ is selected from —OR$^b$, —SR$^b$, —C(O)R$^b$, —NR$^c$R$^d$, —S(O)CHR$^c$R$^d$, —S(O)$_2$CHR$^c$R$^d$, —C(O)NR$^c$R$^d$, phenyl, substituted phenyl, pyridyl, substituted pyridyl, naphthyl, substituted naphthyl, phenoxy, substituted phenoxy, thiophenyl, substituted thiophenyl, morpholinyl, substituted morpholinyl, N-ethyl morpholinyl, substituted N-ethyl morpholinyl, piperazinyl, substituted piperazinyl, 4,5,6,7-tetrahydrothieno[3,2-c]pyridyl, methylphenyl sulfonyl, or substituted methylphenyl sulfonyl;
R$^b$ is methyl, ethyl, propyl, 2-propyl, butyl, tertiary butyl, amyl, substituted C$_{1-8}$ alkyl, phenyl or substituted phenyl; R$^c$ or R$^d$ is independently selected from H, C$_{1-8}$ alkyl, or substituted C$_{1-8}$ alkyl; or R$^c$ and R$^d$ are cyclized to form cycloalkyl, substituted cycloalkyl, a heteroaryl radical, or a substituted heteroaryl radical; and
the substituent is selected from one or more of D, —OH, —NH$_2$, —CN, acyl, halogen, C$_{1-4}$ alkyl, halogenated C$_{1-4}$ alkyl, deuterated C$_{1-4}$ alkyl, or C$_{1-2}$ alkoxy.

9. The compound according to claim 8, wherein,
R$^3$ is selected from —OR$^b$, —SR$^b$, —C(O)R$^b$, —NR$^c$R$^d$, —S(O)$_2$CHR$^c$R$^d$, —C(O)NR$^c$R$^d$, phenyl, substituted phenyl, pyridyl, substituted pyridyl, naphthyl, substituted naphthyl, quinolyl, substituted quinolyl, thiophenyl, substituted thiophenyl, phenoxy, substituted phenoxy, pyridylthio, morpholinyl, piperazinyl, substituted piperazinyl, or 4,5,6,7-tetrahydrothieno[3,2-c]pyridyl;
R$^b$ is methyl, ethyl, propyl, 2-propyl, butyl, tertiary butyl, amyl, substituted C$_{1-8}$ alkyl, phenyl or substituted phenyl; R$^c$ or R$^d$ is independently selected from H, C$_{1-8}$ alkyl, or substituted C$_{1-8}$ alkyl; or R$^c$ and R$^d$ are cyclized to form cycloalkyl, substituted cycloalkyl, a heteroaryl radical, or a substituted heteroaryl radical; and
the substituent is selected from one or more of D, —OH, —CN, —NH$_2$, —NHCH$_3$, —F, —Cl, —Br, —CH$_3$, —CH$_2$CH$_3$, —CHDCH$_2$D, —CF$_3$, —OCH$_3$, or —OCH$_2$CH$_3$.

10. The compound according to claim 1, wherein the compound is selected from the following compounds or pharmaceutically acceptable salts thereof:
2-(3-cyano-4-ethoxyphenyl)-4-methyl-selenazole-5-carboxylic acid,
2-(3-cyano-4-isopropoxyphenyl)-4-methyl-selenazole-5-carboxylic acid,
2-[3-cyano-4-(3-methyl-butoxy)phenyl]-4-methyl-selenazole-5-carboxylic acid,
2-[3-cyano-4-(cyclohexylmethoxy)phenyl]-4-methyl-selenazole-5-carboxylic acid,
2-[3-cyano-4-(benzyloxy)phenyl]-4-methyl-selenazole-5-carboxylic acid,
2-[3-cyano-4-(cyclopropylmethoxy)phenyl]-4-methyl-selenazole-5-carboxylic acid, 2-(2-cyano-biphenyl-4-yl)-4-methyl-selenazole-5-carboxylic acid,
2-(2-cyano-3',4'-dimethoxybiphenyl-4-yl)-4-methyl-selenazole-5-carboxylic acid,
2-(2-cyano-3'-fluoro-4'-methoxybiphenyl-4-yl)-4-methyl-selenazole-5-carboxylic acid,
2-(2-cyano-3',4',5'-trimethoxybiphenyl-4-yl)-4-methyl-selenazole-5-carboxylic acid,
2-(2-cyano-4'-methoxybiphenyl-4-yl)-4-methyl-selenazole-5-carboxylic acid,
2-(2-cyano-3'-methoxybiphenyl-4-yl)-4-methyl-selenazole-5-carboxylic acid,
2-(2-cyano-3'-trifluoromethoxybiphenyl-4-yl)-4-methyl-selenazole-5-carboxylic acid,
2-(2-cyano-4'-chlorobiphenyl-4-yl)-4-methyl-selenazole-5-carboxylic acid,
2-(2-cyano-3',4'-difluorobiphenyl-4-yl)-4-methyl-selenazole-5-carboxylic acid,
2-(2-cyano-2',3',4',5',6'-pentadeuterobiphenyl-4-yl)-4-methyl-selenazole-5-carboxylic acid,
2-(2-cyano-2'-methoxybiphenyl-4-yl)-4-methyl-selenazole-5-carboxylic acid,
2-(2-cyano-2',4'-dimethoxybiphenyl-4-yl)-4-methyl-selenazole-5-carboxylic acid,
2-[3-cyano-4-(1-naphthyl)-phenyl]-4-methyl-selenazole-5-carboxylic acid,
2-[3-cyano-4-(4-pyridyl)-phenyl-4-yl]-4-methyl-selenazole-5-carboxylic acid,
2-(3-cyano-4-(3-pyridyl)-phenyl-4-yl]-4-methyl-selenazole-5-carboxylic acid,
2-[2-cyano-4'-(1,2-deuteroethyl)-biphenyl-4-yl]-4-methyl-selenazole-5-carboxylic acid,
2-(2-cyano-6-deuterobiphenyl-4-yl)-4-methyl-selenazole-5-carboxylic acid,
2-(3-cyano-4-isopropylthiophenyl)-4-methyl-selenazole-5-carboxylic acid,
2-(3-cyano-4-isobutylthiophenyl)-4-methyl-selenazole-5-carboxylic acid,
2-[3-cyano-4-(4-chrolophenylthio)-phenyl]-4-methyl-selenazole-5-carboxylic acid,
2-[3-cyano-4-(3-trifluoromethylphenylthio)-phenyl]-4-methyl-selenazole-5-carboxylic acid,
2-[3-cyano-4-(2-pyridylthio)-phenyl]-4-methyl-selenazole-5-carboxylic acid,
2-(3-cyano-4-benzylthio-phenyl)-4-methyl-selenazole-5-carboxylic acid,
2-(3-cyano-4-isopropyl sulfone-phenyl)-4-methyl-selenazole-5-carboxylic acid,
2-(3-cyano-4-morpholinyl-4-yl-phenyl)-4-methyl-selenazole-5-carboxylic acid,
2-[3-cyano-4-(4-methylpiperazine-1-yl)phenyl]-4-methyl-selenazole-5-carboxylic acid,
2-{3-cyano-4-(6,7-dihydro-4H-thieno [3,2-c]pyridyl)-phenyl}-4-methyl-selenazole-5-carboxylic acid,
2-(3-cyano-4-dimethylamino-phenyl)-4-methyl-selenazole-5-carboxylic acid,
2-(3-fluoro-4-isobutoxyphenyl)-4-methyl-selenazole-5-carboxylic acid,
2-(3-trifluoromethyl-4-isobutoxyphenyl)-4-methyl-selenazole-5-carboxylic acid,
2-[3-cyano-4-(isopropylthiomethyl)-phenyl]-4-methyl-selenazole-5-carboxylic acid,
2-[3-bromo-4-(aniline formyl)-phenyl]-4-methyl-selenazole-5-carboxylic acid,
2-(2-cyano-4'-trifluoromethylbiphenyl-4-yl)-4-methyl-selenazole-5-carboxylic acid,
2-(2-cyano-3'-trifluoromethylbiphenyl-4-yl)-4-methyl-selenazole-5-carboxylic acid,
2-(2-cyano-2'-trifluoromethylbiphenyl-4-yl)-4-methyl-selenazole-5-carboxylic acid,
2-(3-cyano-4-isobutoxyphenyl)-4-hydroxymethyl-selenazole-5-carboxylic acid,
2-(3-bromo-4-isobutoxyphenyl)-4-methyl-selenazole-5-carboxylic acid,
2-(3-cyano-4-isopropylthiophenyl)-4-methyl-selenazole-5-carboxylic acid-(2-N-acetyl)ethyl ester, 2-(3-cyano-4-tertbutylthiophenyl)-4-methyl-selenazole-5-carboxylic acid, 2-(3-cyano-4-cyclohexylthiophenyl)-4-methyl-selenazole-5-carboxylic acid, or
2-(3-trifluoromethylphenyl)-4-methyl-selenazole-5-carboxylic acid.

11. A pharmaceutical composition, comprising any compound or a pharmaceutically acceptable salt thereof according to claim 1 as an active ingredient.

12. The pharmaceutical composition according to claim 11, for use in the treatment of hyperuricemia, gout, diabetic nephropathy, an inflammatory disease or a neurological disease.

13. A method for inhibiting the activity of xanthine oxidase, the method comprising administering, to an organism in need of such inhibition, an effective amount of the compound or the pharmaceutically acceptable salt of claim 1.

14. The method of claim 13, wherein the organism is a human.

15. A method of reducing uric acid generation, the method comprising administering, to an organism in need of such reduction, an effective amount of the compound or the pharmaceutically acceptable salt of claim 1.

16. The method of claim 15, wherein the organism is a human.

17. A method for the treatment of hyperuricemia, gout, diabetic nephropathy, an inflammatory disease or a neurological disease, the method comprising administering, to an organism in need of such treatment, an effective amount of the compound or the pharmaceutically acceptable salt of claim 1.

18. The method of claim 17, wherein the effective amount of the compound or the pharmaceutically acceptable salt is effective for inhibiting the activity of xanthine oxidase.

19. The method of claim 17, wherein the organism is a human.

20. A method for the treatment of hyperuricemia and gout, the method comprising administering, to an organism in need of such treatment, an effective amount of a xanthine oxidase inhibitor, wherein the xanthine oxidase inhibitor comprises the compound or the pharmaceutically acceptable salt of claim 1.

21. The method of claim 20, wherein the organism is a human.

* * * * *